(12) United States Patent
Suetsugu et al.

(10) Patent No.: US 6,476,024 B1
(45) Date of Patent: Nov. 5, 2002

(54) PYRIDAZINE DERIVATIVES AND RELATED COMPOSITION

(75) Inventors: Masaru Suetsugu, Yokohama (JP); Eijiro Hara, Yokohama (JP); Yuji Matsushita, Yokohama (JP); Haruhiko Inoue, Yokohama (JP); Haruo Ogawa, Yokohama (JP); Keiko Sakai, Yokohama (JP); Shigeru Mugikura, Yokohama (JP)

(73) Assignee: Shiseido Co. Ltd., Tokyo (JP)

( * ) Notice: Subject to any disclaimer, the term of this patent is extended or adjusted under 35 U.S.C. 154(b) by 0 days.

(21) Appl. No.: 10/086,855

(22) Filed: Mar. 4, 2002

Related U.S. Application Data

(62) Division of application No. 09/736,256, filed on Dec. 15, 2000, now Pat. No. 6,395,896.

(30) Foreign Application Priority Data

Dec. 15, 1999 (JP) .............................. 11-356201

(51) Int. Cl.⁷ ........................ A61K 31/5377; A61K 7/42
(52) U.S. Cl. ........................ 514/232.2; 424/59; 424/69; 424/70.9; 514/844; 514/845; 514/937; 544/82; 512/2
(58) Field of Search ................. 514/232.2, 844; 424/59, 69; 544/82; 512/2

(56) References Cited

PUBLICATIONS

M. Yanai et al.: "Studies on the Synthesis of Pyridazine Derivatives. XII. Synthesis of 4,5-Diaminopyridazine Derivatives" Chem.Pharm.Bull., vol. 18, No. 8, 1970, pp. 1680–1684, XP000984098.

I. Sekikawa: "Alkaline Hydrolysis of 1,2,5-Thiadiazole-3, 4-dicarboxylic Acid Bishydrazide" J. Heterocycl. Chem. vol. 6, 1969, pp. 129–130, XP000984618.

*Primary Examiner*—Robert W. Ramsuer
(74) *Attorney, Agent, or Firm*—Fei-Fei Chao; Venable, Baetjer, Howard & Civiletti, LLP

(57) ABSTRACT

Ultraviolet absorbents and photostabilizers have an excellent absorption ability in a wide range of ultraviolet rays, and also have high stability and high safety. The ultraviolet absorbent and photostabilizer include a pyridazine derivative of the formula (1):

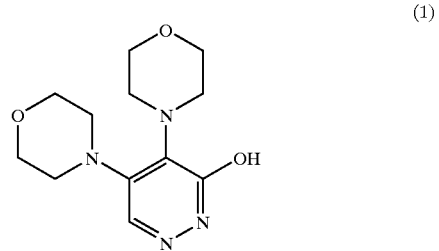

(1)

or salts thereof. Also, described are methods for manufacturing said pyridazine derivative and/or this salts thereof comprising the process of reacting at least 10 wt % of 4,5-dichloro-3-hydroxypyridazine or 4,5-dibromo-3-hydroxypyridazine or mixtures thereof with at least 20 vol % of morpholine in reaction solution at 70° C. or higher. The ultraviolet absorbents photostabilizers include said pyridazine derivative and/or salts thereof as effective ingredient. An ultraviolet ray absorption composition and an external preparation for skin are also included.

12 Claims, 1 Drawing Sheet

PYRIDAZINE DERIVATIVES AND RELATED COMPOSITION

RELATED APPLICATIONS

This application is a divisional application which claims the priority of U.S. patent application Ser. No. 09/736,256, filed on Dec. 15, 2000, now U.S. Pat. No. 6,395,896 which in turn claims the priority of Japanese Patent Application No. 11-356201, filed Dec. 15, 1999. Both the U.S. patent application Ser. No. 09/736,256 and Japanese Patent Application No. 11-356201 are herein incorporated by reference.

FIELD OF THE INVENTION

The present invention relates to pyridazine derivatives, a method for its manufacture, compositions thereof including ultraviolet absorbents and photostabilizers, ultraviolet-ray-absorptive compositions and external preparations for skin.

BACKGROUND OF THE INVENTION

Ultraviolet rays of wavelength 290 nm or less in sunlight are absorbed by the ozone layer. Accordingly, these do not reach the surface of the earth. However, as the ultraviolet rays of 290 to 400 nm reach the surface of the earth, these ultraviolet rays have various effects. In skin chemistry, the ultraviolet rays of the wavelength of 290 nm to 320 nm cause the formation of erythema and blistering. It is known that these ultraviolet rays cause acceleration of melanism and chromatosis. The long wavelength ultraviolet rays of 320 to 400 nm causes the melanism of skin immediately after irradiation. Also, since the energy reaches to an corium of skin, these ultraviolet rays influence the elastica in the walls of blood vessels and connective tissue. These ultraviolet rays of middle wavelength to long wavelength accelerate the aging of skin. Also, it is thought that these ultraviolet rays are a cause of the formation of stains, freckles, wrinkles and the like.

To protect the skin from such ultraviolet rays, ultraviolet absorbents have been used. These ultraviolet absorbents include, for example, benzotriazole derivatives, benzophenone derivatives, salicylic acid derivatives, p-aminobenzoic acid derivatives, cinnamic acid derivatives, and urocanic acid derivatives.

These ultraviolet absorbents are used in photostabilizers of colorant, perfume, drug, etc., in medical supplies and cosmetics.

Also, ultraviolet absorbents are used in fields other than medical supplies and cosmetics. For example, they are added to the various materials of coating, dye, pigment, resin, synthetic rubber, latex, film and fiber. As these are given absorbing ability for ultraviolet rays, a product, or paints or films coating a product can be protected from the ultraviolet rays. The ultraviolet absorbent is used to maintain quality by preventing degradation, degeneration and so on by the ultraviolet rays.

It is desirable that an ultraviolet absorbent is able to absorb the ultraviolet rays of all the wavelength range of 290 nm to 400 nm which reach the surface of the earth. Also, when an ultraviolet absorbent is included in an external preparation for skin, it is important that the ultraviolet absorbent is not decomposed by sunlight exposure. Also, it is important that the ultraviolet absorbent does not cause skin irritation.

However, conventional ultraviolet absorbents do not always satisfy these preferences. Conventional ultraviolet absorbents sometimes cause coloring and deposition due to ultraviolet rays shielding agents in inorganic powders commonly used in external preparations for skin. Also, a satisfactory photostabilizer compound has been needed.

Also, conventional ultraviolet rays absorbents in other fields sublimate and volatilize by heating during sintering of paints and in the forming of resin. In addition, these absorbents vaporize gradually and become less effective with the passing of time, even if it is not heated.

SUMMARY OF THE INVENTION

The present invention is achieved in view of the foregoing prior art. The object of the present invention is to provide an ultraviolet absorbent, a photostabilizer and a manufacturing method, which have an excellent absorbing ability in the wide ultraviolet rays wavelength range, that have high stability and safety. It is a another object of the present invention to provide an ultraviolet ray absorption composition including said ultraviolet absorbent. It is further object of the present invention to provide an external preparation for skin including said ultraviolet absorbent or said photostabilizer.

As a result of diligent study by the present inventors, it was found that a certain kind of pyridazine derivatives have the above-mentioned properties and are excellent ultraviolet absorbents and photostabilizers.

Namely, the present invention is pyridazine derivatives of general formula (1) and salts thereof. The compound of the present invention has excellent absorbing ability with respect to the wide ultraviolet ray wavelength range. As it is very stable and safe, it is an excellent ultraviolet absorbent and photostabilizer.

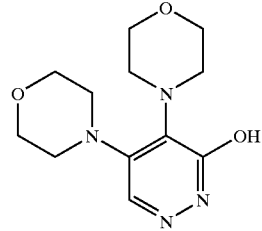

(1)

A manufacturing method of the pyridazine derivatives comprises the process of reacting at least 10 wt % of 4,5-Dichloro-3-hydroxypyridazine or 4,5-Dibromo-3-hydroxypyridazine or combination thereof, with at least 20 vol % of morpholine in a reaction solution at 70° C. or higher.

An ultraviolet absorbent of the present invention comprises said pyridazine derivatives and/or salts thereof as an active ingredient.

An ultraviolet ray absorption composition of the present invention includes said ultraviolet absorbents.

A photostabilizer of the present invention comprises said pyridazine derivatives and/or salts thereof, as an active ingredient. It is preferable that said photostabilizer includes a sequestering agent.

An external preparation for skin of the present invention comprises said ultraviolet absorbents. Also, it is preferable that the external preparation for skin of the present invention includes an inorganic powder.

Also, an external preparation for skin of the present invention comprises said photostabilizer. It is preferable that said external skin preparation includes a sequestering agent.

Also, in the external skin preparation of the present invention, it is preferable that said external preparation for skin includes 0.001 wt % to 20 wt % of said pyridazine derivatives or salts thereof.

DETAILED DESCRIPTION OF THE PREFERRED EMBODIMENT

Pyridazine Derivatives and Salts Thereof

Figure 1:
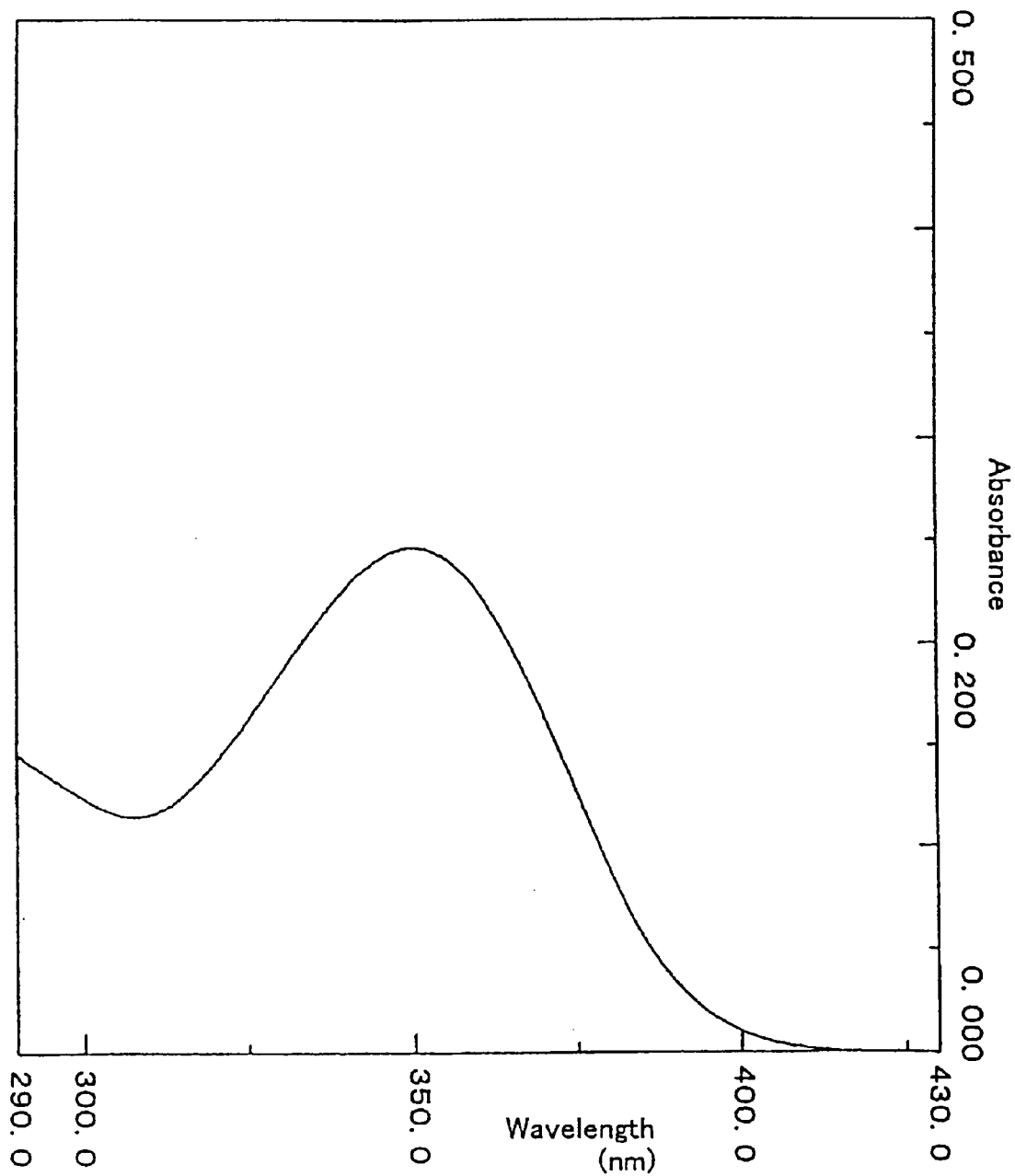
FIG. 1 shows the ultraviolet absorption spectrum of pyridazine derivative (4,5-Dimorpholino-3-hydroxypyridazine) of the present invention.

A pyridazine derivative of the present invention is shown in a general formula (1). This compound can be isomerized to general formula (1'), which is tautomer with the equilibrium like the following, under certain conditions.

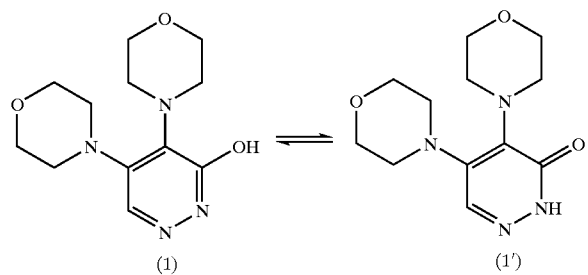

The pyridazine derivatives in the present invention are described only by the general formula (1) for convenience. However, the pyridazine derivatives in the present invention can be isomerized to a general formula (1') as a tautomer.

The chemical name of the pyridazine derivative of the present invention includes 4,5-Dimorpholino-3-hydroxypyridazine and 4,5-Dimorpholino-3-hydroxypyridazine hydrochloride and the like.

A pyridazine derivative of the present invention can be synthesized by the followings method.

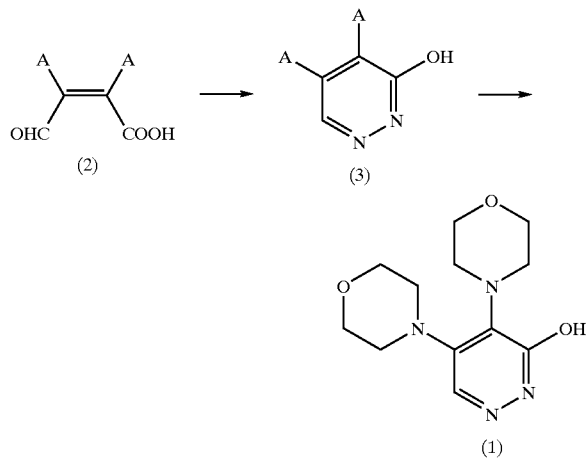

In the above-mentioned reaction formula, A represents a chlorine atom or bromine atom. The compound of a general formula (3) (when A is a chlorine atom, 4,5-Dichloro-3-hydroxypyridazine; when A is a bromine atom, 4,5-Dibromo-3-hydroxypyridazine) can be synthesized by the method of Chemische Berichte, 32, 543(1899) and so on in accordance with the above-mentioned formula. The compounds of the general formula (2) can be easily available.

Namely, the compounds of a general formula (3) is easily obtained by cyclic reaction of compounds of a general formula (2) and hydrazine. Also, the compounds of the general formula (3) (A is chlorine atom) which can be available from ALDRICH Inc. Also, pyridazine derivatives of the present invention were obtained by reacting 10 wt % or more of a compound of the general formula (3) and 20 vol % or more of morpholine in a reaction solution at 70° C. or higher. In the case where the concentration of compounds of the general formula (3) in the reaction solution is less than 10 wt %, in the case where the concentration of morpholine in the reaction solution is less than 20 vol %, and in the case where reaction temperature is lower than 70° C., it was difficult to obtain pyridazine derivatives of the present invention.

Also, the pyridazine derivatives of the present invention include inorganic acid salt or organic acid salt made by published methods. Examples of inorganic acids include hydrochloric acid, sulfuric acid, phosphoric acid, hydrobromic acid. Examples of organic acids include acetic acid, lactic acid, maleic acid, fumaric acid, tartaric acid, citric acid, methanesulfonic acid, p-toluenesulfonic acid.

Ultraviolet Absorbent and External Preparation for Skin

An ultraviolet absorbent having as its principal component pyridazine derivative or salt thereof can be included in various products. An external skin preparation including this absorbent is suitable. An external preparation for skin having the ultraviolet absorbent of the present invention demonstrates an excellent ultraviolet ray prevention effect. Also, since the ultraviolet absorbent does not decompose under sunlight exposure, the effect is continued for a long time. Also, it does not cause problems for the skin. Accordingly, it is especially useful as the external skin preparation for sun screen.

Also, to increase the ultraviolet rays shielding effect in an external skin preparation for sun screen, it is preferred that an ultraviolet absorbent of an organic compound and an ultraviolet ray shielding agent of an inorganic powder are included. Also, many cosmetics for makeup include inorganic powder. However, use of an organic ultraviolet absorbent and inorganic powder may cause discoloration.

The ultraviolet absorbent of the present invention does not cause discoloration, when included with an inorganic powder in an external skin preparation for skin. Therefore, it is possible to include inorganic powder.

Inorganic Powder

In the present invention, an inorganic powder includes powder in cosmetics and medical supplies. Examples of inorganic powder include talc, kaolin, boron nitride, mica, sericite, muscovite, black mica, golden mica, synthetic mica, vermiculite, magnesium carbonate, calcium carbonate, silicic anhydride, aluminum silicate, aluminum oxide, barium silicate, calcium silicate, magnesium cilicate, tungsten metal salt, magnesium, silica, zeolite, barium sulfate, calcined calcium sulfate, calcined gypsum, calcium phosphate, fluoroapatite, calcium phosphate hydroxide, ceramic powder, metal soap (zinc myristate, calcium palmitate, aluminum stearate etc.). Also, examples of inorganic pigment include titanium dioxide, zinc oxide, iron oxide, iron titanium oxide, carbon, low-valent titanium oxide, mango violet, cobalt violet, chromium oxide, chromium hydroxide, cobalt titanium oxide, ultramarine, iron blue, titanium oxide coated mica, titanium oxide coated bismuth oxychloride, colored titanium oxide coated mica, bismuth oxychloride, fish scale flake.

Photostabilizer

The pyridazine derivatives and salts thereof of the present invention are useful as a photostabilizer. Especially, the compound is an excellent photostabilizer of colorants, perfumes and drugs in medical supplies and cosmetics. Also, the pyridazine derivatives and salts thereof of the present invention can achieve a synergistic photostabilization effect, by including a sequestering agent.

Sequestering Agent

In the present invention, pyridazine derivatives or salts thereof can be used with a sequestering agent. Examples of sequestering agents include sodium ethylenediaminetetraacetate (EDTA), trisodium hydroxyethyl ethylenediamine triacetate(dihydrate), phosphoric acid, citric acid, ascorbic acid, succinic acid, gluconic acid, sodium polyphosphate, sodium metaphosphate, 1-hydroxyethane 1,1-diphosphate.

Use of External Preparation for Skin

The external preparation for skin of the present invention may includes the above-mentioned ultraviolet absorbent or the above-mentioned photostabilizer. Forms of the external preparation for skin of the present invention are not restricted if the effect of the present invention is demonstrated. Examples of forms of the external preparation for skin of the present invention include lotion, milky lotion, cream and essence for skin care cosmetics. Also, examples of makeup cosmetics include base cosmetics, foundation, lipstick, face color and eyeliner. Also, examples of cosmetics for hair and scalp include hair spray, hair tonic and hair liquid.

Amount of Pyridazine Derivative or Salts Thereof in an External Skin Preparation When the external preparation for skin includes the pyridazine derivatives and/or salts thereof of the present invention, the amount depends on the need for UV absorbing ability or photostabilization ability. Usually the preferable amount of pyridazine derivative and/or salt thereof in a composition is 0.001 wt % to 20 wt %, more preferably 0.01 wt % to 10 wt %. If the amount is less than 0.001 wt %, the ultraviolet rays prevention effect or photostabilization effect may inadequate. Also, if the amount is more than 20 wt %, it may be difficult to maintain the form of external skin preparation.

Other Ingredients

The external preparation for skin of the present invention can include other ingredients often included in cosmetics and medical supplies. Examples of other ingredients include liquid fat and oil, solid fat and oil, wax, hydrocarbon, higher fatty acid, higher alcohol, ester, silicone, anionic surfactant, cationic surfactant, ampholytic surfactants, nonionic surfactant, humectants, water-soluble high molecular compounds, thickeners film formers, lower alcohol, polyhydric alcohol, saccharides, amino acid, organic amine, pH adjustment agent, skin nutrition agents, vitamins, antioxidants, perfumes, powder, colorants and water and the like. These ingredients can be combined in external preparation for skin of the present invention if needed. Also, ultraviolet absorbents and photostabilizers other than the pyridazine derivatives of the present invention can be combined unless the objects of the invention are thwarted.

Ultraviolet Absorptive Composition

The ultraviolet absorbent of the present invention can be used in products other than external skin preparation. For example, coating, dye, pigment, resin, synthetic rubber, latex, film, fiber and so on can include the ultraviolet absorbent of the present invention for ultraviolet ray prevention. Since pyridazine derivatives of the present invention excel in heat stability without vaporizing, the effect can be maintained for a long time. The preferable amount in this case is usually 0.001 wt % to 20 wt %, more preferably 0.01 wt % to 10 wt %. If the amount is less than 0.001 wt %, the ultraviolet ray defense effect may be inadequate. If the amount is greater than 20 wt %, it may be difficult to form of the external skin preparation.

The present invention is explained in more fully by the following examples, but, the present invention is not restricted to these examples. The following are the manufacturing examples of pyridazine derivatives of the present invention.

1. A method synthesizing a 4,5-Dimorphorino-3-hydroxypyridazine 4,5-Dichloro-3-hydroxypyridazine (25.0 g, 0.151 mol= about 17 wt % in reaction solusion) was dissolved to morpholine (120 ml=100 vol %). The mixture was heated at 70° C. or more for 24 hours. After being cooled, deposited crystal was filtered. White crystal of 4,5-Dimorpholibo-3-hydroxypyridazine (37.2 g, yield percentage 92%) was obtained.

Melting point 256 to 257° C. (Decomposition) (Capil.)

Next, chemical analysis values of the obtained compound were shown. Table 1 shows the result of elemental analysis. Next, the results of $^1$H-NMR, $^{13}$C-NMR and MS spectra were shown. These chemical data support the desired compound.

TABLE 1

| Elemental analysis value | C (%) | H (%) | N (%) |
|---|---|---|---|
| Calcd.(*) (%) | 54.12 | 6.81 | 21.04 |
| Found (%) | 54.25 | 6.72 | 21.11 |

*Calcd. for $C_{12}H_{18}N_4O_3$ $^1$H-NMR (DMSO-$d_6$, TMS, ppm) δ:3.21 (dd, 4H, J=4.4&4.9Hz: —CH$_2$—N—CH$_2$—), 3.23 (dd, 4H, J=4.4&4.9Hz: —CH$_2$—N—CH$_2$—), 3.62 (dd, 4H, J=4.4&4.9Hz: —CH$_2$—O—CH$_2$—), 3.70 (dd, 4H, J=4.4&4.9Hz: —CH$_2$—O—CH$_2$—), 7.67 (s, 1H: pyridazine ring H-6), 12.38 (s, 1H: OH)

$^{13}$C-NMR: (DMSO-$d_6$, TMS, ppm) δ:47.8 (—CH$_2$—N—CH$_2$—), 48.5 (—CH$_2$—N—CH$_2$—), 66.1 (—CH$_2$—O—CH$_2$—), 66.6 (—CH$_2$—O—CH$_2$—), 131.1, 132.6, 141.0 (pyridazine ring C-4, C-5, C-6), 160.7 (pyridazine ring C-3)

MS spectrum: MW=266 ($C_{12}H_{18}N_4O_3$=266.30)

2. A method synthesizing a 4,5-Dimorpholino-3-hydroxyPyridazine 4,5-Dibromo-3-hydroxypyridazine (25.0 g, 0.098 mol= about 17 wt % in reaction solution) was dissolved to morpholine (120 ml=100 vol %). The mixture was heated at 70° C. or higher for 24 hours. After being cooled, deposited crystal was filtered. White crystal of 4,5-Dimorpholibo-3-hydroxypyridazine (23.7 g, yield percentage 90%) was obtained.

Melting point 256 to 257° C. (Decomposition) (Capil.)

Next, chemical analysis values for the obtained compound are shown. Table 2 shows the result of elementary analysis. Next, the results of $^1$H-NMR, $^{13}$C-NMR and MS spectra were shown. These chemical data support the desired components.

TABLE 2

| Elemental analysis value | C (%) | H (%) | N (%) |
|---|---|---|---|
| Calcd.(*) (%) | 54.12 | 6.81 | 21.04 |
| Found (%) | 54.22 | 6.82 | 21.09 |

*Calcd. for $C_{12}H_{18}N_4O_3$ $^1$H-NMR (DMSO-$d_6$, TMS, ppm) δ:3.21 (dd, 4H, J=4.4&4.9Hz: —CH$_2$—N—CH$_2$—), 3.23 (dd, 4H, J=4.4&4.9Hz: —CH$_2$—N—CH$_2$—), 3.62 (dd, 4H, J=4.4&4.9Hz: —CH$_2$—O—CH$_2$—), 3.70 (dd, 4H, J=4.4&4.9Hz: —CH$_2$—O—CH$_2$—), 7.67 (s, 1H: pyridazine ring H-6), 12.38 (s, 1H:OH)

$^{13}$C-NMR: (DMSO-d$_6$, TMS, ppm) δ:47.8 (—CH$_2$—N—CH$_2$—), 48.5 (—CH$_2$—N—CH$_2$—), 66.1 (—CH$_2$—O—CH$_2$—), 66.6 (—CH$_2$—O—CH$_2$—), 131.1, 132.6, 141.0 (pyridazine ring C-4, C-5, C-6), 160.7 (pyridazine ring C-3)

MS spectrum: MW=266 (C$_{12}$H$_{18}$N$_4$O$_3$=266.30)

Next, test result for ultraviolet rays absorbing ability of the pyridazine derivatives of the present invention are shown.

Test 1 Absorption

Ultraviolet rays absorption spectrum of 4,5-Dimorpholino-3-hydroxypyridazine (Solvent: water, Concentration: 10 ppm, Light path: 1 cm) was measured by the spectrophotometer (Manufactured by Nihonbunko Inc., Trade name: Ubest-55). The result was shown in FIG. 1.

FIG. 1 shows that a pyridazine derivative of the present invention can absorb strongly with respect to the entire wavelength range of ultraviolet rays, 290 nm to 400 nm, which reach the surface of the earth. Also, it shows hardly any absorption in visible range for wavelengths longer than 400 nm. Accordingly, pyridazine derivatives of the present invention is excellent in visual transparency.

Test Example 2 Ultraviolet Rays Prevention Effect (i) Test method

The prevention effect test was carried out on a beach during the summer. Equal amounts of sample were applied to the right and left sides of the backs of test subjects. After direct sunlight exposure, the degree of sunburn was evaluated in accordance with the following criteria. Each group consisted of 20 subjects.

(Criterion)

Remarkable effect: None or almost no sunburn symptom was found.

Positive effect: Slight sunburn symptom was found.

Negative effect: Strong sunburn symptom was found.

(Evaluation)

A: Subject of remarkable effect or positive effect is 80% or more.

B: Subject of remarkable effect or positive effect is 50% or more and less than 80%.

C: Subject of remarkable effect or positive effect is 30% or more and less than 50%.

D: Subject of remarkable effect or positive effect is less than 30%

(ii) Preparation of sample (A) Lotion (Alcohol phase)

| | |
|---|---|
| 95% Ethanol | 25.0 (wt %) |
| Polyoxyethylene(25) hydrogenated castor oil | 2.0 |
| Ultraviolet absorbent (See Table 3) | 0 to 20 |
| Antiseptics | q.s. |
| Perfume | q.s. |

(Water phase)

| | |
|---|---|
| Glycerol | 5.0 |
| Sodium hexametaphosphate | q.s. |
| Ion-exchanged water | Balance |

(Manufacturing method)

Each of water phase and alcohol phase was prepared. Then each was mixed.

(B) Cream

| | |
|---|---|
| Stearyl alcohol | 7.0 (wt %) |
| Stearic acid | 2.0 |
| Hydrogenated lanolin | 2.0 |
| Squalane | 5.0 |
| 2-Octyldodecyl alcohol | 6.0 |
| Polyoxyethylene(25) cetyl ether | 3.0 |
| Glyceryl monostearate | 2.0 |
| Propylene glycol | 5.0 |
| Ultraviolet absorbent(See Table 4) | 0 to 20 |
| Perfume | q.s. |
| Sodium hydrogensulfite | 0.03 |
| Ethyl paraben | 0.3 |
| Ion-exchanged water | Balance |

(Manufacturing method)

The propylene glycol was added to ion-exchanged water and was dissolved, which was kept at 70° C. by heating (Water phase). The other components were mixed and melted by heating and was kept at 70° C. (Oil phase). The oil phase was added to the water phase, and an emulsion was formed. After it was homogeneously emulsified with a homomixer, it was cooled at 30° C. with stirring well.

(iii) Result

The result with regard to lotion (a), cream (b) were shown in Table 3 and 4, respectively.

TABLE 3

| Ultraviolet absorbent | Amount (wt %) | UV prevent effect |
|---|---|---|
| 4,5-dimorpholino-3-hydroxypyridazine | 20 | A |
| | 10 | A |
| | 5 | A |
| | 1 | A |
| | 0.01 | A |
| | 0.001 | B |
| | 0.0005 | C |
| No combination | 0 | D |

TABLE 4

| Ultraviolet absorbent | Amount (wt %) | UV prevent effect |
|---|---|---|
| 4,5-dimorpholino-3-hydroxypyridazine | 20 | A |
| | 10 | A |
| | 5 | A |
| | 1 | A |
| | 0.1 | A |
| | 0.001 | B |
| | 0.0005 | C |
| No combination | 0 | D |

Table 3 and Table 4 show that external skin preparation including a pyridazine derivative of the present invention has excellent ultraviolet ray prevention effect as an ultraviolet absorbent. Also, it shows that the preferable amount of pyridazine derivative and/or salt thereof of the present invention is 0.001 wt % to 20 wt %. Also, having an amount greater than 20 wt % makes it difficult to form an external skin preparation.

Accordingly, the pyridazine derivatives of the present invention have excellent absorbing ability with regard to wide range of ultraviolet rays. The inventors have studied with regard to the amount of pyridazine derivative of the present invention in an ultraviolet absorbent in external skin preparation The inventors have studied it with regard to skin irritation, photostability and inorganic powder.

Test Example 3 Skin Irritation Test

Sample (10 wt % of ultraviolet absorbent) is the same as test example 2.

(i) Continuous use test

The continuous use test by the healthy subjects was carried out with one group of twenty subjects. A proper amount of each sample was applied to the face twice a day for 4 weeks. The evaluation standard of Table 5 was judged.

TABLE 5

| Degree of skin reaction | Score |
| --- | --- |
| No symptom (Negative) | 0 |
| Very slight symptom (false negative) | 1 |
| Slight symptom (weak positive) | 2 |
| Middle symptom (middle positive) | 3 |
| Strong symptom (strong positive) | 4 |

(Evaluation)

The calculated average score was evaluated by the next standard.

A: Average score is 0.
B: Average score is over 0 and less than 1.
C: Average score is 1 or more, and less than 2.
D: Average score is 2 or more.
The result was shown in Table 6.

TABLE 6

| Ultraviolet absorbent | Formulation | Judgment |
| --- | --- | --- |
| 4,5-dimorpholino-3-hydroxypyridazine | Lotion | A |
|  | Cream | A |
| No combination | Lotion | A |
|  | Cream | A |

(ii) Patch test

An occlusive patch test was carried out in the antebrachium part of healthy men and women subjects by finchamber for 24 hours. Each group was twenty subjects. The judgement standard is shown in Table 7.

TABLE 7

| Degree of skin reaction | Score |
| --- | --- |
| No reaction (Negative) | 0 |
| Slight erythema (false positive) | 1 |
| Erythema (weak positive) | 2 |
| Erythema + edema (Middle degree positive) | 3 |
| Erythema + edema + papula (Strong positive) | 4 |
| Erythema bullosum (Most strong positive) | 5 |

(Evaluation)

Each of the calculated average scores was evaluated by the following evaluation standard.

A: average score is 0.
B: average score is over 0 and less than 1.
C: average score is 1 or more and less than 2.
D: average score is 2 or more.
The results was shown in Table 8.

TABLE 8

| Ultraviolet absorbent | Formulation | Judgment |
| --- | --- | --- |
| 4,5-dimorpholino-3-hydroxypyridazine | Lotion | A |
|  | Cream | A |
| No combination | Lotion | A |
|  | Cream | A |

Table 6 and Table 8 shows that external preparation for skin including ultraviolet absorbent of the present invention does not cause skin irritation in continuous use test and patch test. Also, it is understood that external preparation for skin of the present is very safe.

Test example 4 Photostability test

After an aqueous solution of the pyridazine derivative of the present invention was exposed to sunlight (Amount of solar radiation exposure $80MJ/m^2$) for two weeks, residual yield and change of appearance were checked. UV absorption spectrum (Solvent: water, concentration: 10 ppm, Light path: 1 cm) was measured by spectrophotometer. Area value was calculated by integrating over the range of 290 nm to 400 nm of the ultraviolet rays absorption spectrum. The area value was compared with the value before sunlight exposure.

(Evaluation standard)

The residual yield and change of area value of ultraviolet rays absorption spectrum were evaluated by the following standard.

A: 95% or more of area value before sunlight exposure.
B: 90% or more and less than 95% of area value before sunlight exposure.
C: 70% or more and less than 90% of area value before sunlight exposure.
D: less than 70% of area value before sunlight exposure.
The result was shown in Table 9.

TABLE 9

| Ultraviolet absorbent | Residual yield | Change of area value of UV absorption spectrum |
| --- | --- | --- |
| 4,5-dimorpholino-3-hydroxypyridazine | A | A |

Table 9 shows that a pyridazine derivative of the present invention has a very high residual yield. Accordingly, pyridazine derivative of the present invention did not decomposed by direct sunlight exposure for a long time. Also, the shape and area value of ultraviolet ray absorption spectrum did not change. Also, coloring and deposition and so on in the appearance were not found.

Test Example 6 Stability Test in Case of Including UV Shielding Agent of Inorganic Powder The sun screen cream of the following formulation was manufactured. These were preserved for 2 months at 50° C. By visual observation of discoloration, the inventors have checked stability when using an UV shielding agent of inorganic powder which is included as external skin preparation for the ultraviolet rays defense.

(Formulation)

| Sun-screen cream | |
|---|---|
| (1) Ethyl cellulose | 1.0 (wt %) |
| (2) Ethanol | 5.0 |
| (3) 2-Ethylhexyl succinate | 24.0 |
| (4) Titanium dioxide | 1.0 |
| (5) Porous silicic anhydride powder | 1.0 |
| (6) Spherical nylon powder | 1.0 |
| (7) Talc | 1.0 |
| (8) Sericite | 1.0 |
| (9) Boron nitride | 1.0 |
| (10) Silicone treated mica | 1.0 |
| (11) Ultraviolet absorbent (See Table 10) | 10.0 |
| (12) Carboxymethylcellulose | 1.0 |
| (13) Ion-exchanged water | Balance |
| (14) Antiseptics | q.s. |
| (15) Perfume | q.s. |

(Manufacturing method)

After (2) was added to (1) and was swelled sufficiently, (3) to (11) was added thereto and was mixed with heating. The mixture was sufficiently dissolved with dispersing. This dispersed liquid was kept at 70° C. After this dispersed liquid was emulsified homogeneously by homomixer with adding a mixture of (12) to (15) gradually, which was cooled to 30° C. with stirring well to obtain sun screen.

The result was shown in Table 10.

TABLE 10

| Ultraviolet absorbent | Discoloration |
|---|---|
| 4,5-Dimorpholino-3-hydroxypyridazine | No |

Table 10 shows that discoloration is not found in a pyridazine derivative of the the present invention in the case where inorganic powder is used.

Accordingly, pyridazine derivatives of the present invention do not cause skin irritation and excel in photostability. Also, discoloration does not result in case of use of inorganic powder. Accordingly, pyridazine derivatives of the present invention are very useful as an ultraviolet absorbent in an external skin preparation.

Next, the effect as a photostabilizer of pyridazine derivative of the present invention was studied.

First of all, the photostabilization effect and appearance change of a composition in each pigment were studied by the following evaluation formulation.

| Formulation for evaluation of colorant stabilization effect | |
|---|---|
| Material | Amount (wt %) |
| Ion-exchanged water | to 100 |
| Brucine denatured alcohol | 5 |
| Glycerol | 5 |
| Dipropylene glycol | 5 |
| Polyoxyethylene hydrogenated castor oil | 1 |
| Methyl paraben | 0.2 |
| Lactic acid | 0.006 |
| Sodium lactate | 0.2 |
| Photo-stabilizer (See Table 11 to 16) | See Table 11 to 16 |
| Pigment (See Table 11 to 16) | See Table 11 to 16 |
| Total | 100 |

Each test sample was prepared. Observation of appearance change (visual evaluation) and measurement of color difference ($\Delta E$) were carried out in samples exposed to sunlight exposure (around 80MJ).

Color difference was measured by Lab coordinate system with spectrophotometer. Color difference was calculated on the basis of the color before sunlight exposure. Namely, from measured value $(L_1, a_1, b_1)$ before sunlight exposure, color difference ($\Delta E$) was calculated by following formula.

$$\Delta E = \{(L_2-L_1)^2+(a_2-a_1)^2+(b_2-b_1)^2\}^{1/2}$$

Table 11 and Table 12 show the result of the combination of a single colorant and various kinds of photostabilizer.

TABLE 11

| Test example | Colorant Name | Amount | Photostabilizer Name | Amount | Sunlight exposure (80 MJ) $\Delta E$ | Appearance |
|---|---|---|---|---|---|---|
| 7 | Red No. 227 | 0.0001 | No | 0 | 1.45 | C |
| 8 | (D & C Red No. 33) | | 4,5-Dimorpholino-3-hydroxypyridazine | 0.05 | 0.49 | A |
| 9 | (Trade name: Fast Acid Magenta) | | 2-Hydroxy-4-methoxybenzophenone | 0.05 | 0.71 | B |
| 10 | | | 2-Hydroxy-4-methoxybenzophenone-5-sodium sulfonate | 0.05 | 0.80 | B |
| 11 | | | Octyl-p-methoxycinnamate | 0.05 | 1.22 | C |
| 12 | | | 4-tert-Butyl-4'-methoxy-di-benzoylmethane | 0.05 | 0.95 | B |
| 13 | Red No. 106 | 0.0001 | No | 0 | 3.04 | C |
| 14 | (Trade name: Acid Red 52) | | 4,5-Dimorpholino-3-hydroxypyridazine | 0.05 | 0.82 | A |
| 15 | | | 2-Hydroxy-4-methoxybenzophenone | 0.05 | 1.01 | B |
| 16 | | | 2-Hydroxy-4-methoxybenzophenone-5-sodium sulfonate | 0.05 | 0.98 | B |
| 17 | | | Octyl p-methoxycinnamate | 0.05 | 1.95 | C |
| 18 | | | 4-tert-Butyl-4'-methoxy-di-benzoylmethane | 0.05 | 1.02 | B |
| 19 | Yellow No. 203 | 0.001 | No | 0 | 2.77 | C |
| 20 | (D & C Yellow No. 52) | | 4,5-Dimorpholino-3-hydroxypyridazine | 0.05 | 0.18 | A |
| 21 | (Trade name: Quinoline Yellow WS) | | 2-Hydroxy-4-methoxybenzophenone | 0.05 | 0.88 | B |
| 22 | | | 2-Hydroxy-4-methoxybenzophenone-5-sodium sulfonate | 0.05 | 0.76 | B |
| 23 | | | Octyl p-methoxycinnamate | 0.05 | 2.43 | C |
| 24 | | | 4-tert-Butyl-4'-methoxy-di-benzoylmethane | 0.05 | 0.68 | B |
| 25 | Yellow No. 5 | 0.001 | No | 0 | 1.83 | C |
| 26 | (FD & C Yellow No. 6) | | 4,5-Dimorpholino-3-hydroxypyridazine | 0.05 | 0.43 | A |
| 27 | (Trade name: Sunset Yellow FCF) | | 2-Hydroxy-4-methoxybenzophenone | 0.05 | 0.82 | B |
| 28 | | | 2-Hydroxy-4-methoxybenzophenone-5-sodium sulfonate | 0.05 | 0.78 | B |

TABLE 11-continued

| Test example | Colorant Name | Amount | Photostabilizer Name | Amount | Sunlight exposure (80 MJ) ΔE | Appearance |
|---|---|---|---|---|---|---|
| 29 | | | Octyl p-methoxycinnamate | 0.05 | 1.56 | C |
| 30 | | | 4-tert-Butyl-4'-methoxy-di-benzoylmethane | 0.05 | 0.88 | B |

Appearance(Evaluation by vision) A: No change B: No almost change C: Yes change

TABLE 12

| Test example | Colorant Name | Amount | Photostabilizer Name | Amount | Sunlight exposure (80MJ) ΔE | Appearance |
|---|---|---|---|---|---|---|
| 31 | Blue No. 1 | 0.0001 | No | 0 | 8.92 | C |
| 32 | (FD & C Blue No. 1) | | 4,5-Morpholino-3-hydroxypyridazine | 0.05 | 1.11 | A |
| 33 | (Trade name: Brilliant Blue FCF) | | 2-Hydroxy-4-methoxybenzophenone | 0.05 | 1.76 | B |
| 34 | | | 2-Hydroxy-4-methoxybenzophenone-5-sodium sulfonate | 0.05 | 1.67 | B |
| 35 | | | Octyl p-methoxycinnamate | 0.05 | 5.23 | C |
| 36 | | | 4-tert-Butyl-4'-methoxy-di-benzoylmethane | 0.05 | 1.49 | B |
| 37 | Green No. 3 | 0.0001 | No | 0 | 2.12 | C |
| 38 | (FD & C Green No. 3) | | 4,5-Dimorpholino-3-hydroxypyridazine | 0.05 | 0.31 | A |
| 39 | (Trade name: Fast Green FCF) | | 2-Hydroxy-4-methoxybenzophenone | 0.05 | 0.75 | B |
| 40 | | | 2-Hydroxy-4-methoxybenzophenone-5-sodium sulfonate | 0.05 | 0.74 | B |
| 41 | | | Octyl p-methoxycinnamate | 0.05 | 1.64 | C |
| 42 | | | 4-tert-Butyl-4'-methoxy-di-benzoylmethane | 0.05 | 0.62 | B |
| 43 | Red No. 213 | 0.0001 | No | 0 | 3.79 | C |
| 44 | (D & C Red No. 19) | | 4,5-Dimorpholino-3-hydroxypyridazine | 0.05 | 0.78 | A |
| 45 | (Trade name: Rhodamine B) | | 2-Hydroxy-4-methoxybenzophenone | 0.05 | 1.34 | B |
| 46 | | | 2-Hydroxy-4-methoxybenzophenone-5-sodium sulfonate | 0.05 | 1.28 | B |
| 47 | | | Octyl p-methoxycinnamate | 0.05 | 2.55 | C |
| 48 | | | 4-tert-Butyl-4'-methoxy-di-benzoylmethane | 0.05 | 1.02 | B |
| 49 | Red No. 401 | 0.001 | No | 0 | 7.58 | C |
| 50 | (Ext. D & C Red No. 3) | | 4.5-Dimorpholino-3-hydroxypyridazine | 0.05 | 0.71 | A |
| 51 | (Trade name: Violamine R) | | 2-Hydroxy-4-methoxybenzophenone | 0.05 | 1.18 | B |
| 52 | | | 2-Hydroxy-4-methoxybenzophenone-5-sodium sulfonate | 0.05 | 1.39 | B |
| 53 | | | Octyl p-methoxycinnamate | 0.05 | 4.76 | C |
| 54 | | | 4-tert-Butyl-4'-methoxy-di-benzoylmethane | 0.05 | 1.02 | B |

Appearance(Evaluation by vision) A: No change B: No almost change C: Yes change

Next, Table 13 shows the result of the combination of multiple pigments and various kinds of photostabilizer.

TABLE 13

| Test example | Colorant Name | Amount | Photostabilizer Name | Amount | Sunlight exposure (80 MJ) ΔE | Appearance |
|---|---|---|---|---|---|---|
| 55 | Red No. 227 | 0.0001 | No | 0 | 1.59 | C |
| 56 | (Trade name: Fast Acid Magenta) | 0.0001 | 4,5-Dimorpholino-3-hydroxypyridazine | 0.05 | 0.59 | A |
| 57 | Yellow No. 5 | | 2-Hydroxy-4-methoxybenzophenone | 0.05 | 0.88 | B |
| 58 | (Trade name: Sunset Yellow FCF) | | 4-tert-Butyl-4'-methoxy-di-benzoylmethane | 0.05 | 0.80 | B |
| 59 | Red No. 227 | 0.0001 | No | 0 | 3.05 | C |
| 60 | (Trade name: Fast Acid Magenta) | 0.0001 | 4,5-Dimorpholino-3-hydroxypyridaxine | 0.05 | 0.78 | A |
| 61 | Yellow No. 203 | | 2-Hydro-4-methoxybenzophenone | 0.05 | 1.05 | B |
| 62 | (Trade name: Quinoline Yellow WS) | | 4-tert-Butyl-4'-methoxybenzophenone | 0.05 | 1.12 | B |
| 63 | Red No. 106 | 0.00001 | No | 0 | 3.77 | C |
| 64 | (Trade name: Acid Red 52) | 0.0001 | 4,5-Dimorpholino-3-hydroxypyridazine | 0.05 | 0.77 | A |
| 65 | Yellow No. 203 | | 2-Hydroxy-4-methoxybenzophenone | 0.05 | 1.11 | B |
| 66 | (Trade name: Quinoline Yellow WS) | | 4-tert-Butyl-4'-methoxy-di-benzoylmethane | 0.05 | 1.02 | B |
| 67 | Red No. 106 | 0.00001 | No | 0 | 4.45 | C |
| 68 | (Trade name: Acid Red 52) | 0.0001 | 4,5-Dimorpholino-3-hydroxypyridazine | 0.05 | 0.55 | A |
| 69 | Yellow No. 5 | | 2-Hydroxy-4-methoxybenzophenone | 0.05 | 1.18 | B |
| 70 | (Trade name: Sunset Yellow FCF) | | 4-tert-Butyl-4'-methoxy-di-benzoylmethane | 0.05 | 0.92 | B |
| 71 | Yellow No. 203 | 0.0001 | No | 0 | 1.45 | C |
| 72 | (Trade name: Quinoline Yellow WS) | 0.0001 | 4,5-Dimorpholino-3-hydroxypyridazine | 0.05 | 0.37 | A |
| 73 | Yellow No. 5 | | 2-Hydro-4-methoxybenzophenone | 0.05 | 0.52 | A |
| 74 | (Trade name: Sunset Yellow FCF) | | 4-tert-Butyl-4'-methoxy-di-benzoylmethane | 0.05 | 0.48 | A |
| 75 | Red No. 213 | 0.00001 | No | 0 | 3.89 | C |
| 76 | (Trade name: Rhodamine B) | 0.00001 | 4,5-Dimorpholino-3-hydroxypyridazine | 0.05 | 0.97 | A |
| 77 | Blue No. 1 | | 2-Hydro-4-methoxybenzophenone | 0.05 | 1.26 | B |
| 78 | (Trade name: Brilliant Blue FCF) | | 4-tert-Butyl-4'-methoxy-di-benzoylmethane | 0.05 | 1.17 | B |

TABLE 13-continued

| Test example | Colorant Name | Amount | Photostabilizer Name | Amount | Sunlight exposure (80 MJ) ΔE | Appearance |
|---|---|---|---|---|---|---|
| 79 | Red No. 401 | 0.0001 | No | 0 | 3.04 | C |
| 80 | (Trade name: Violamine R) | 0.00001 | 4,5-Dimorpholino-3-hydroxypyridazine | 0.05 | 0.32 | A |
| 81 | Blue No.1 | | 2-Hydro-4-methoxybenzophenone | 0.05 | 0.82 | B |
| 82 | (Trade name: Brilliant Blue FCF) | | 4-tert-Butyl-4'-methoxy-di-benzoylmethane | 0.05 | 0.93 | B |
| 83 | Red No. 431 | 0.0001 | No | 0 | 4.54 | C |
| 84 | (Trade name: Violamine R) | 0.00001 | 4,5-Dimorpholino-3-hydroxypyridazine | 0.05 | 0.73 | A |
| 85 | Green No. 3 | | 2-Hydro-4-methoxybenzophenone | 0.05 | 1.06 | B |
| 86 | (Trade name: Fast Green FCF) | | 4-tert-Butyl-4'-methoxy-di-benzoylmethane | 0.05 | 0.99 | B |

Appearance(Evaluation by vision) A: No change B: No almost change C: Yes change

Tables 11 to 13 show that the color difference ΔE in a pyridazine derivative (4,5-dimorpholino-3-hydroxypyridazine) of the present invention is very small in comparison with other photostabilizers. Also, the change of appearance of the composition is small. Accordingly, it is understood that pyridazine derivative of the present invention has excellent photo stability for colorant.

Next, the inventors studied the effective amount of photostabilizer of the present invention for pigment. Table 14 and Table 15 show the result of combination of a pyridazine derivative of the present invention and a single colorant.

TABLE 14

| Test example | Colorant Name | Amount | Photostabilizer Name | Amount | Sunlight exposure (80 MJ) ΔE | Apperance |
|---|---|---|---|---|---|---|
| 87 | Red No. 227 | 0.0001 | 4,5-Dimorpholino-3-hydroxypyridazine | 0 | 1.45 | C |
| 88 | (D & C Red No. 33) | | | 0.02 | 0.71 | A |
| 89 | (Trade name: Fast Acid Magenta) | | | 0.05 | 0.49 | A |
| 90 | | | | 0.1 | 0.22 | A |
| 91 | | 0.00001 | | 0 | 2.35 | C |
| 92 | | | | 0.05 | 0.69 | A |
| 93 | | | | 0.1 | 0.32 | A |
| 94 | | | | 0.3 | 0.11 | A |
| 95 | Red No. 106 | 0.0001 | 4,5-Dimorpholino-3-hydroxypyridazine | 0 | 3.04 | C |
| 96 | (Trade name: Acid Red 52) | | | 0.03 | 0.95 | A |
| 97 | | | | 0.05 | 0.82 | A |
| 98 | | | | 0.1 | 0.43 | A |
| 99 | | 0.00001 | | 0 | 4.54 | C |
| 100 | | | | 0.05 | 1.01 | A |
| 101 | | | | 0.1 | 0.55 | A |
| 102 | | | | 0.3 | 0.12 | A |
| 103 | Yellow No. 203 | 0.001 | 4,5-Dimorpholino-3-hydroxypyridazine | 0 | 2.77 | C |
| 104 | (D & C Yellow No. 10) | | | 0.02 | 0.25 | A |
| 105 | (Trade name: Quinoline Yellow WS) | | | 0.05 | 0.18 | A |
| 106 | | | | 0.1 | 0.08 | A |
| 107 | | 0.0001 | | 0 | 3.52 | C |
| 108 | | | | 0.05 | 0.22 | A |
| 109 | | | | 0.1 | 0.10 | A |
| 110 | | | | 0.3 | 0.05 | A |
| 111 | Yellow No. 5 | 0.001 | 4,5-Dimorpholino-3-hydroxypyridazine | 0 | 1.83 | C |
| 112 | (FD & C Yellow No. 6) | | | 0.01 | 0.61 | A |
| 113 | (Trade name: Sunset Yellow FCF) | | | 0.05 | 0.43 | A |
| 114 | | | | 0.1 | 0.22 | A |
| 115 | | 0.0001 | | 0 | 2.54 | C |
| 116 | | | | 0.05 | 0.59 | A |
| 117 | | | | 0.1 | 0.71 | A |
| 118 | | | | 0.3 | 0.22 | A |

Appearance(Evaluation by vision) A: No change B: No almost change C: Yes change

TABLE 15

| Test example | Colorant Name | Amount | Photostabilizer Name | Amount | Sunlight exposure (80 MJ) ΔE | Apperance |
|---|---|---|---|---|---|---|
| 119 | Blue No. 1 | 0.0001 | 4,5-Dimorpholino-3-hydroxypyridazine | 0 | 8.92 | C |
| 120 | (FD & C Blue No. 1) | | | 0.03 | 1.25 | A |
| 121 | (Trade name: Brilliant Blue FCF) | | | 0.05 | 1.11 | A |
| 122 | | | | 0.1 | 0.70 | A |

TABLE 15-continued

| Test example | Colorant | | Photostabilizer | | Sunlight exposure (80 MJ) | |
|---|---|---|---|---|---|---|
| | Name | Amount | Name | Amount | ΔE | Apperance |
| 123 | | 0.00001 | | 0 | 8.02 | C |
| 124 | | | | 0.05 | 1.00 | A |
| 125 | | | | 0.1 | 0.62 | A |
| 126 | | | | 0.3 | 0.25 | A |
| 127 | Green No. 3 | 0.0001 | 4,5-Dimorpholino-3-hydroxypyridazine | 0 | 2.12 | C |
| 128 | (FD & C Green No. 3) | | | 0.02 | 0.75 | A |
| 129 | (Trade name: Fast Green FCF) | | | 0.05 | 0.31 | A |
| 130 | | | | 0.1 | 0.06 | A |
| 131 | | 0.00001 | | 0 | 3.02 | C |
| 132 | | | | 0.03 | 0.56 | A |
| 133 | | | | 0.1 | 0.08 | A |
| 134 | | | | 0.3 | 0.02 | A |
| 135 | Red No. 213 | 0.0001 | 4,5-Dimorpholino-3-hydroxypyridazine | 0 | 3.79 | C |
| 136 | (D & C Red No. 19) | | | 0.03 | 1.11 | B |
| 137 | (Trade name: Rhodamine B) | | | 0.05 | 0.78 | A |
| 138 | | | | 0.1 | 0.32 | A |
| 139 | | 0.00001 | | 0 | 4.57 | C |
| 140 | | | | 0.03 | 1.24 | B |
| 141 | | | | 0.1 | 0.45 | A |
| 142 | | | | 0.3 | 0.12 | A |
| 143 | Red No. 401 | 0.001 | 4,5-Dimorpholino-3-hydroxypuridazine | 0 | 7.58 | C |
| 144 | (Ext. D & C Red No. 3) | | | 0.03 | 0.95 | A |
| 145 | (Trade name: Violamine R) | | | 0.05 | 0.71 | A |
| 146 | | | | 0.1 | 0.45 | A |
| 147 | | 0.0001 | | 0 | 8.28 | C |
| 148 | | | | 0.05 | 0.82 | A |
| 149 | | | | 0.1 | 0.56 | A |
| 150 | | | | 0.3 | 0.19 | A |

Appearance(Evaluation by vision) A: No change B: No almost change C: Yes change

Table 16 shows the result of combining a pyridazine derivative of the present invention and multiple colorant.

TABLE 16

| Test example | Colorant | | Photostabilizer | | Sunlight exposure (80 MJ) | |
|---|---|---|---|---|---|---|
| | Name | Amount | Name | Amount | ΔE | Apperance |
| 151 | Red No. 227 | 0.0001 | 4,5-Dimorpholino-3-hydroxypyridazine | 0 | 1.59 | C |
| 152 | (Trade name: Fast Acid Magenta) | 0.0001 | | 0.03 | 0.72 | A |
| 153 | Yellow No. 5 | | | 0.05 | 0.59 | A |
| 154 | (Trade name: Sunset Yellow FCF) | | | 0.1 | 0.18 | A |
| 155 | Red No. 227 | 0.0001 | 4,5-Dimorpholino-3-hydroxypyridazine | 0 | 3.05 | C |
| 156 | (Trade name: Fast Acid Magenta) | 0.0001 | | 0.05 | 0.78 | A |
| 157 | Yellow No. 203 | | | 0.1 | 0.35 | A |
| 158 | (Trade name: Quinoline Yellow WS) | | | 0.3 | 0.14 | A |
| 159 | Red No. 106 | 0.00001 | 4,5-Dimorpholino-3-hydroxyoyridazine | 0 | 3.77 | C |
| 160 | (Trade name: Acid Red 52) | 0.0001 | | 0.05 | 0.77 | A |
| 161 | Yellow No. 203 | | | 0.1 | 0.25 | A |
| 162 | (Trade name: Quinoline Yellow WS) | | | 0.3 | 0.11 | A |
| 163 | Red No. 106 | 0.00001 | 4,5-Dimorpholino-3-hydroxyoyridazine | 0 | 4.45 | C |
| 164 | (Trade name: Acid Red 52) | 0.0001 | | 0.03 | 0.97 | A |
| 165 | Yellow No. 5 | | | 0.05 | 0.55 | A |
| 166 | (Trade name: Sunset Yellow FCF) | | | 0.3 | 0.12 | A |
| 167 | Yellow No. 203 | 0.0001 | 4,5-Dimorpholino-3-hydroxyoyridazine | 0 | 1.45 | C |
| 168 | (Trade name: Quinoline Yellow WS) | 0.0001 | | 0.03 | 0.52 | A |
| 169 | Yellow No. 5 | | | 0.05 | 0.37 | A |
| 170 | (Trade name: Sunset Yellow FCF) | | | 0.1 | 0.12 | A |
| 171 | Red No. 213 | 0.00001 | 4,5-Dimorpholino-3-hydroxyoyridazine | 0 | 3.89 | C |
| 172 | (Trade name: Rhodamine B) | 0.00001 | | 0.03 | 1.21 | A |
| 173 | Blue No. 1 | | | 0.05 | 0.97 | A |
| 174 | (Trade name: Brilliant Blue FCF) | | | 0.1 | 0.73 | A |
| 175 | Red No. 401 | 0.0001 | 4,5-Dimorpholino-3-hydroxyoyridazine | 0 | 3.04 | C |
| 176 | (Trade name: Violamine B) | 0.00001 | | 0.03 | 0.95 | A |
| 177 | Blue No. 1 | | | 0.05 | 0.32 | A |
| 178 | (Trade name: Brilliant Blue FOF) | | | 0.1 | 0.07 | A |
| 179 | Red No. 401 | 0.0001 | 4,5-Dimorpholino-3-hydroxyoyridazine | 0 | 4.54 | C |
| 180 | (Trade name: Violamine R) | 0.00001 | | 0.03 | 0.98 | A |

TABLE 16-continued

| Test example | Colorant | | Photostabilizer | | Sunlight exposure (80 MJ) | | |
|---|---|---|---|---|---|---|---|
| | Name | Amount | Name | Amount | ΔE | Apperance | |
| 181 | Green No. 3 | | | 0.05 | 0.73 | A | |
| 182 | (Trade name: Fast Green FCF) | | | 0.3 | 0.14 | A | |

Appearance(Evaluation by vision) A: No change B: No almost change C: Yes change

Tables 14 to 16 show that approximately 0.01 wt % to approximately 0.3 wt % of pyridazine derivatives of the present invention is effective as a photostabilizer in approximately 0.00001 wt % to approximately 0.001 wt % of colorant. Also, although over 0.3 wt % of pyridazine derivative is possible, in case of external prepalation for skin, if the amount is greater than 20 wt % of pyridazine derivative, it is difficult to maintain the formulation of the external skin preparation.

Next, the photostabilization effect for each perfume was studied by the following evaluation formulation.

Formulation for evaluation of perfume stabilization effect

| Material | Amount (wt %) |
|---|---|
| Ion-exchanged water | to 100 |
| Brucine denatured alcohol | 5 |
| Glycerol | 5 |
| Dipropylene glycol | 5 |
| Polyoxyethylene hydrogenated castor oil | 1 |
| Methyl paraben | 0.2 |
| Lactic acid | 0.006 |
| Sodium lactate | 0.2 |
| Photo-stabilizer (See Table 17 to 22) | See Table 17 to 22 |
| Perfume (See Table 17 to 22) | 0.03 |
| Total | 100 |

Each test sample was prepared. Change of smell of sample exposed to sunlight (80MJ) was observed (judgement by perfumier).

Table 17 shows the result of combining of natural perfume and various photostabilizers.

TABLE 17

| Test example | Natural perfume Name | Photostabilizer Name | Amount | Sunlight exposure (80 MJ) Smell evaluation |
|---|---|---|---|---|
| 183 | Rose oil | No | 0 | C |
| 184 | | 4,5-Dimorpholino-3-hydroxypyridazine | 0.05 | A |
| 185 | | 2-Hydroxy-4-methoxybenzophenone | 0.05 | B |
| 186 | | 2-Hydroxy-4-methoxybenzophenone-5-sodium sulfonate | 0.05 | B |
| 187 | | Octyl p-methoxycinnamate | 0.05 | C |
| 188 | | 4-tert-Butyl-4'-methoxy-di-benzoylmethane | 0.05 | B |
| 189 | Jasmine oil | No | 0 | C |
| 190 | | 4,5-Dimorpholino-3-hydroxypyridazine | 0.05 | A |
| 191 | | 2-Hydroxy-4-methoxybenzophenone | 0.05 | B |
| 192 | | 2-Hydroxy-4-methoxybenzophenone-5-sodium sulfonate | 0.05 | B |
| 193 | | Octyl p-methoxycinnamate | 0.05 | C |
| 194 | | 4-tert-Butyl-4'-methoxy-di-benzoylmethane | 0.05 | B |
| 195 | Neroli oil | No | 0 | C |
| 196 | | 4,5-Dimorpholino-3-hydroxypyridazine | 0.1 | A |
| 197 | | 2-Hydroxy-4-methoxybenzophenone | 0.1 | B |
| 198 | | 2-Hydroxy-4-methoxybenzophenone-5-sodium sulfonate | 0.1 | B |
| 199 | | Octyl p-methoxycinnamate | 0.1 | C |
| 200 | | 4-tert-Butyl-4'-methoxy-di-benzoylmethane | 0.1 | B |
| 201 | Lavender oil | No | 0 | C |
| 202 | | 4,5-Dimorpholino-3-hydroxypyridazine | 0.1 | A |
| 203 | | 2-Hydroxy-4-methoxybenzophenone | 0.1 | B |
| 204 | | 2-Hydroxy-4-methoxybenzophenone-5-sodium sulfonate | 0.1 | B |
| 204 | | Octyl p-methoxycinnamate | 0.1 | C |
| 205 | | 4-tert-Butyl-4'-methoxy-di-benzoylmethane | 0.1 | B |
| 206 | Ylang ylang oil | No | 0 | C |
| 207 | | 4,5-Dimorpholino-3-hydroxypyridazine | 0.2 | A |
| 208 | | 2-Hydroxy-4-methoxybenzophenone | 0.2 | B |
| 209 | | 2-Hydroxy-4-methoxybenzophenone-5-sodium sulfonate | 0.2 | B |
| 210 | | Octyl p-methoxycinnamate | 0.2 | C |
| 211 | | 4-tert-Butyl-4'-methoxy-di-benzoylmethane | 0.2 | B |

Smell evaluation A: No change B: No almost change C: Yes change

Table 17 shows that the change of smell in a pyridazine derivative (4,5-dimorpholino-3-hydroxypyridazine) of the present invention is very small in comparison with other photostabilizers. Accordingly, it is understood that pyridazine derivative of the present invention has an excellent photostabilization effect for natural purfume.

Table 18 shows the result of combining synthetic perfume and various photostabilizers.

TABLE 18

| Test example | Natural perfume Name | Photostabilizer Name | Amount | Sunlight exposure (80 MJ) Smell evaluation |
|---|---|---|---|---|
| 212 | Limonene | No | 0 | C |
| 213 | | 4,5-Dimorpholino-3-hydroxypyridazine | 0.05 | A |
| 214 | | 2-Hydroxy-4-methoxybenzophenone | 0.05 | B |
| 215 | | 2-Hydroxy-4-methoxybenzophenone-5-sodium sulfonate | 0.05 | B |
| 216 | | Octyl p-methoxycinnamate | 0.05 | C |
| 217 | | 4-tert-Butyl-4'-methoxy-di-benzoylmethane | 0.05 | B |
| 218 | Linalool | No | 0 | C |
| 219 | | 4,5-Dimorpholino-3-hydroxypyridazine | 0.05 | A |
| 220 | | 2-Hydroxy-4-methoxybenzophenone | 0.05 | B |
| 221 | | 2-Hydroxy-4-methoxybenzophenone-5-sodium sulfonate | 0.05 | B |
| 222 | | Octyl p-methoxycinnamate | 0.05 | C |
| 223 | | 4-tert-Butyl-4'-methoxy-di-benzoylmethane | 0.05 | B |
| 224 | Citral | No | 0 | C |
| 225 | | 4,5-Dimorpholino-3-hydroxypyridazine | 0.1 | A |
| 226 | | 2-Hydroxy-4-methoxybenzophenone | 0.1 | B |
| 227 | | 2-Hydroxy-4-methoxybenzophenone-5-sodium sulfonate | 0.1 | B |
| 228 | | Octyl p-methoxycinnamate | 0.1 | C |
| 229 | | 4-tert-Butyl-4'-methoxy-di-benzoylmethane | 0.1 | B |
| 230 | Linalyl acetate | No | 0 | C |
| 231 | | 4,5-Dimorpholino-3-hydroxypyridazine | 0.1 | A |
| 232 | | 2-Hydroxy-4-methoxybenzophenone | 0.1 | B |
| 233 | | 2-Hydroxy-4-methoxybenzophenone-5-sodium sulfonate | 0.1 | B |
| 234 | | Octyl p-methoxycinnamate | 0.1 | C |
| 235 | | 4-tert-Butyl-4'-methoxy-di-benzoylmethane | 0.1 | B |
| 236 | Rose oxide | No | 0 | C |
| 237 | | 4,5-Dimorpholino-3-hydroxypyridazine | 0.2 | A |
| 236 | | 2-Hydroxy-4-methoxybenzophenone | 0.2 | B |
| 239 | | 2-Hydroxy-4-methoxybenzophenone-5-sodium sulfonate | 0.2 | B |
| 240 | | Octyl p-methoxycinnamate | 0.2 | C |
| 241 | | 4-tert-Butyl-4'-methoxy-di-benzoylmethane | 0.2 | B |

Smell evaluation A: No change B: No almost change C: Yes change

Table 18 shows that the change of smell in a pyridazine derivative (4,5-dimorpholino-3-hydroxypyridazine) of the present invention is very small in comparison with other photostabilizers. Accordingly, it is understood that pyridazine derivatives of the present invention have an excellent photostabilization effect for synthetic purfume.

Table 19 shows the result of combining base perfume and various photostabilizers.

TABLE 19

| Test example | Base perfume Name | Photostabilizer Name | Amount | Sunlight exposure (80 MJ) Smell evaluation |
|---|---|---|---|---|
| 242 | Rose | No | 0 | C |
| 243 | | 4,5-Dimorpholino-3-hydroxypyridazine | 0.05 | A |
| 244 | | 2-Hydroxy-4-methoxybenzophenone | 0.05 | B |
| 245 | | 2-Hydroxy-4-methoxybenzophenone-5-sodium sulfonate | 0.05 | B |
| 246 | | Octyl p-methoxycinnamate | 0.05 | C |
| 247 | | 4-tert-Butyl-4'-methoxy-di-benzoylmethane | 0.05 | B |
| 248 | Muguet | No | 0 | C |
| 249 | | 4,5-Dimorpholino-3-hydroxypyridazine | 0.05 | A |
| 250 | | 2-Hydroxy-4-methoxybenzophenone | 0.05 | B |
| 251 | | 2-Hydroxy-4-methoxybenzophenone-5-sodium sulfonate | 0.05 | B |
| 252 | | Octyl p-methoxycinnamate | 0.05 | C |
| 253 | | 4-tert-Butyl-4'-methoxy-di-benzoylmethane | 0.05 | B |
| 254 | Woody | No | 0 | C |
| 255 | | 4,5-Dimorpholino-3-hydroxypyridazine | 0.1 | A |
| 256 | | 2-Hydroxy-4-methoxybenzophenone | 0.1 | B |
| 257 | | 2-Hydroxy-4-methoxybenzophenone-5-sodium sulfonate | 0.1 | B |
| 258 | | Octyl p-methoxycinnamate | 0.1 | C |

TABLE 19-continued

| Test example | Base perfume Name | Photostabilizer Name | Amount | Sunlight exposure (80 MJ) Smell evaluation |
|---|---|---|---|---|
| 259 | | 4-tert-Butyl-4'-methoxy-di-benzoylmethane | 0.1 | B |
| 300 | Fruity | No | 0 | C |
| 301 | | 4,5-Dimorpholino-3-hydroxypyridazine | 0.1 | A |
| 302 | | 2-Hydroxy-4-methoxybenzophenone | 0.1 | B |
| 303 | | 2-Hydroxy-4-methoxybenzophenone-5-sodium sulfonate | 0.1 | B |
| 304 | | Octyl p-methoxycinnamate | 0.1 | C |
| 305 | | 4-tert-Butyl-4'-methoxy-di-benzoylmethane | 0.1 | B |
| 306 | Spicy | No | 0 | C |
| 307 | | 4,5-Dimorpholino-3-hydroxypyridazine | 0.2 | A |
| 308 | | 2-Hydroxy-4-methoxybenzophenone | 0.2 | B |
| 309 | | 2-Hydroxy-4-methoxybenzophenone-5-sodium sulfonate | 0.2 | B |
| 310 | | Octyl p-methoxycinnamate | 0.2 | C |
| 311 | | 4-tert-Butyl-4'-methoxy-di-benzoylmethane | 0.2 | B |

Smell evaluation A: No change B: No almost change C: Yes change

Table 19 shows that the change of smell in a pyridazine derivative (4,5-dimorpholino-3-hydroxypyridazine) of the present invention is very small in comparison with other photostabilizers. Accordingly, it is understood that pyridazine derivatives of the present invention have an excellent photo stabilization effect for base perfume.

Next, the inventors have studied the effective amount of photostabilizer for perfume. Table 20 shows the result of combining a pyridazine derivative of the present invention and natural perfume.

TABLE 20

| Test example | Natural perfume Name | Photostabilizer Name | Amount | Sunlight exposure (80MJ) Smell evaluation |
|---|---|---|---|---|
| 312 | Tuberose oil | 4,5-Dimorpholino-3-hydroxypyridazine | 0.03 | A |
| 313 | | | 0 | C |
| 314 | Clary sage oil | | 0.03 | A |
| 315 | | | 0 | C |
| 316 | Cloves oil | | 0.03 | A |
| 317 | | | 0 | C |
| 318 | Peppermint oil | | 0.03 | A |
| 319 | | | 0 | C |
| 320 | Geranium oil | | 0.03 | A |
| 321 | | | 0 | C |
| 322 | Patchouli oil | | 0.01 | A |
| 323 | | | 0 | C |
| 324 | Sandals wood oil | | 0.01 | A |
| 325 | | | 0 | C |
| 326 | Cinnamon oil | | 0.01 | A |
| 327 | | | 0 | C |
| 328 | Coriander oil | | 0.01 | A |
| 329 | | | 0 | C |
| 330 | Nutmeg oil | | 0.01 | A |
| 331 | | | 0 | C |
| 332 | Pepper oil | | 0.001 | A |
| 333 | | | 0 | C |
| 334 | Lemon oil | | 0.001 | A |
| 335 | | | 0 | C |
| 336 | Orange oil | | 0.1 | A |
| 337 | | | 0 | C |
| 338 | Bergamot oil | | 0.1 | A |
| 339 | | | 0 | C |
| 340 | Opopanax oil | | 0.1 | A |
| 341 | | | 0 | C |
| 342 | Vetiver oil | | 0.2 | A |
| 343 | | | 0 | C |
| 344 | Orris oil | | 0.2 | A |
| 345 | | | 0 | C |
| 346 | Oakmoss oil | | 0.2 | A |
| 347 | | | 0 | C |
| 348 | Musk oil | | 0.2 | A |
| 349 | | | 0 | C |
| 350 | Civet oil | | 0.2 | A |
| 351 | | | 0 | C |
| 352 | Castoreum oil | | 0.3 | A |
| 353 | | | 0 | C |
| 354 | Ambergris oil | | 0.3 | A |
| 355 | | | 0 | C |

Smell evaluation A: No change B: No almost change C: Yes change

Table 20 shows that approximately 0.001 wt % to approximately 0.3 wt % of a pyridazine derivative of the present invention is effective as a photostabilizer in approximately 0.03 wt % of natural perfume.

Next, Table 21 shows the result of combining a pyridazine derivative of the present invention and synthetic perfume.

TABLE 21

| Test example | Synthetic perfume Name | Photostabilizer Name | Amount | Sunlight exposure (80MJ) Smell evaluation |
|---|---|---|---|---|
| 356 | β-Caryophyllene | 4,5-Dimorpholino-3-hydroxypyridazine | 0.01 | A |
| 357 | | | 0 | C |
| 358 | cis-3-Hexonol | | 0.01 | A |
| 359 | | | 0 | C |
| 360 | Farnesol | | 0.01 | A |
| 361 | | | 0 | C |
| 362 | β-Phenyletheyl alcohol | | 0.03 | A |
| 363 | | | 0 | C |
| 364 | 2,6-Nonadienal | | 0.03 | A |
| 365 | | | 0 | C |
| 366 | α-Hexyl cinnamic aldehyde | | 0.03 | A |
| 367 | | | 0 | C |
| 368 | β-Ionone | | 0.05 | A |
| 369 | | | 0 | C |
| 370 | l-Carvone | | 0.05 | A |
| 371 | | | 0 | C |
| 372 | Cyclopentadecanone | | 0.05 | A |

TABLE 21-continued

| Test example | Synthetic perfume Name | Photostabilizer Name | Amount | Sunlight exposure (80MJ) Smell evaluation |
|---|---|---|---|---|
| 373 | | | 0 | C |
| 374 | Benzyl benzoate | | 0.1 | A |
| 375 | | | 0 | C |
| 376 | γ-Undecalactone | | 0.1 | A |
| 377 | | | 0 | C |
| 378 | Eugenol | | 0.1 | A |
| 379 | | | 0 | C |
| 380 | Indole | | 0.2 | A |
| 381 | | | 0 | C |
| 382 | Phenylacetaldehyde | | 0.2 | A |
| 383 | dimethyl acetal | | 0 | C |
| 386 | Lyral | | 0.3 | A |
| 387 | | | 0 | C |
| 388 | Lilial | | 0.3 | A |
| 389 | | | 0 | C |

Smell evaluation A: No change B: No almost change C: Yes change

Table 21 shows that approximately 0.01 wt % to approximately 0.3 wt % of a pyridazine derivative of the present invention is effective as a photostabilizer for approximately 0.03 wt % of synthetic perfume.

Next, Table 22 shows the result of combining a pyridazine derivative of the present invention and a base perfume.

TABLE 22

| Test example | Base perfume Name | Photostabilizer Name | Amount | Sunlight exposure (80MJ) Smell evaluation |
|---|---|---|---|---|
| 390 | Jasmine | 4,5-Dimorpholio-3-hydroxypyridazine | 0.01 | A |
| 391 | | | 0 | C |
| 392 | Chypre | | 0.01 | A |
| 393 | | | 0 | C |
| 394 | Citrus | | 0.03 | A |
| 395 | | | 0 | C |
| 396 | Green | | 0.05 | A |
| 397 | | | 0 | C |
| 398 | Fougere | | 0.1 | A |
| 399 | | | 0 | C |

TABLE 22-continued

| Test example | Base perfume Name | Photostabilizer Name | Amount | Sunlight exposure (80MJ) Smell evaluation |
|---|---|---|---|---|
| 400 | Oriental | | 0.1 | A |
| 401 | | | 0 | C |
| 402 | Aldehyde | | 0.2 | A |
| 403 | | | 0 | C |
| 404 | Animal | | 0.3 | A |
| 405 | | | 0 | C |

Smell evaluation A: No change B: No almost change C: Yes change

Table 22 shows that approximately 0.01 wt % to approximately 0.3 wt % of a pyridazine derivative of the present invention is effective as a photostabilizer for approximately 0.03 wt % of base perfume.

Next, the photo stabilization effect and changed in appearance in drug compositions were studied according to the following evaluation formulation.

Formulation for evaluation of drug stabilization effect

| Material | Amount (wt %) |
|---|---|
| Ion-exchanged water | to 100 |
| Brucine denatured alcohol | 5 |
| Glycerol | 5 |
| Dipropylene glycol | 5 |
| Polyoxyethylene hydrogenated castor oil | 1 |
| Methyl paraben | 0.2 |
| Lactic acid | 0.006 |
| Sodium lactate | 0.2 |
| Stabilizer (See Table 23) | See Table 23 |
| Drug (See Table 23) | See Table 23 |
| Total | 100 |

Each test sample was prepared. Appearance changes of the samples exposed to sunlight (80MJ) was observed (visual evaluation). Also, residual yield was measured by liquid chromatography.

Next, Table 23 shows the result of combining a pyridazine derivative of the present invention and a drug.

TABLE 23

| Test Example | Drug Name | Amount | Photostabilizer Name | Amount | Sunlight exposure (80 MJ) Residual yield (%) | Appearance |
|---|---|---|---|---|---|---|
| 406 | Salicylic acid | 0.1 | No | 0 | 87.6 | C |
| 407 | | | 4,5-Dimorpholino-3-hydroxypyridazine | 0.05 | 100.3 | A |
| 408 | | | 2-Hydroxy-4-methoxybenzophenone | 0.05 | 98.2 | B |
| 409 | | | 2-Hydroxy-4-methoxybenzophene-5-sodium sulfonate | 0.05 | 98.0 | B |
| 410 | | | Octyt p-methoxycinnamate | 0.05 | 92.2 | C |
| 411 | | | 4-tert-Butyl-4'-methoxy-di-benzoylmethane | 0.05 | 97.2 | B |
| 412 | Dipotassium glcyrrhizinate | 0.05 | No | 0 | 85.1 | C |
| 413 | | | 4,5-Dimorpholino-3-hydroxypyridazine | 0.05 | 100.3 | A |
| 414 | | | 2-Hydroxy-4-methoxybenzophenone | 0.05 | 97.8 | B |
| 415 | | | 2-Hydroxy-4-methoxybenzophene-5-sodium sulfonate | 0.05 | 97.5 | B |
| 416 | | | Octyt p-methoxycinnamate | 0.05 | 90.8 | C |
| 417 | | | 4-tert-Butyl-4'-methoxy-di-benzoylmethane | 0.05 | 96.6 | B |
| 418 | L-ascorbic acid 2-(dl-α-α-tocopheryl) | 0.01 | No | 0 | 69.0 | C |

TABLE 23-continued

| Test Example | Drug Name | Amount | Photostabilizer Name | Amount | Residual yield (%) | Sunlight expoxure (80 MJ) Appearance |
|---|---|---|---|---|---|---|
| 419 | hydrogen phosphate) potassium salt | | 4,5-Dimorpholino-3-hydroxypyridazine | 0.05 | 99.4 | A |
| 420 | | | 2-Hydroxy-4-methoxybenzophenone | 0.05 | 95.4 | B |
| 421 | | | 2-Hydroxy-4-methoxybenzophene-5-sodium sulfonate | 0.05 | 95.0 | B |
| 422 | | | Octyt p-methoxycinnamate | 0.05 | 82.1 | C |
| 423 | | | 4-tert-Butyl-4'-methoxy-di-benzoylmethane | 0.05 | 94.5 | B |
| 424 | 2-o-α-α-glucopyranosyl- | 2.0 | No | 0 | 84.7 | C |
| 425 | L-ascorbic acid | | 4,5-Dimorpholino-3-hydroxypyridazine | 0.05 | 99.3 | A |
| 426 | | | 2-Hydroxy-4-methoxybenzophenone | 0.05 | 97.8 | B |
| 427 | | | 2-Hydroxy-4-methoxybenzophene-5-sodium sulfonate | 0.05 | 97.3 | B |
| 428 | | | Octyt p-methoxycinnamate | 0.05 | 92.3 | C |
| 429 | | | 4-tert-Butyl-4'-methoxy-di-benzoylmethane | 0.05 | 97.0 | B |
| 430 | Dibutylhydroxytoluene | 0.01 | No | 0 | 48.0 | C |
| 431 | | | 4,5-Dimorpholino-3-hydroxypyridazine | 0.05 | 98.8 | A |
| 432 | | | 2-Hydroxy-4-methoxybenzophenone | 0.05 | 95.2 | B |
| 433 | | | 2-Hydroxy-4-methoxybenzophene-5-sodium sulfonate | 0.05 | 94.8 | B |
| 434 | | | Octyt p-methoxycinnamate | 0.05 | 71.7 | C |
| 435 | | | 4-tert-Butyl-4'-methoxy-di-benzoylmethane | 0.05 | 95.2 | B |

Appearance A: No change  B: No almost change  C: Yes change

Table 23 shows that residual yield of a drug combined with a pyridazine derivative (4,5-dimorpholino-3-hydroxypyridazine) of the present invention is very high in comparison with other photostabilizers. Also, appearance changes of the composition is small. Accordingly, it is understood that pyridazine derivatives of the present invention have an excellent photostabilization effect on drugs.

The inventors have attempted to improve the photostabilization effect by combining the composition with sequestering agent.

First of all, the photostabilization effect and appearance changes of a composition for each pigment were studied by the following evaluation formulation.

| Formulation for evaluation of pigment stabilization effect (Sequestering agent combination) | |
|---|---|
| Material | Amount (wt %) |
| Ion-exchanged water | to 100 |
| Brucine denatured alcohol | 5 |
| Glycerol | 5 |
| Dipropylene glycol | 5 |
| Polyoxyethylene hydrogenated castor oil | 1 |
| Methyl paraben | 0.2 |
| Lactic acid | 0.006 |
| Sodium lactate | 0.2 |

-continued

| Formulation for evaluation of pigment stabilization effect (Sequestering agent combination) | |
|---|---|
| Material | Amount (wt %) |
| Sequestering agent(See Table 24 to 26) | See Table 24 to 26 |
| 4,5-Dimorpholino-3-hydroxypyridazine | See Table 24 to 26 |
| Pigment(See Table 24 to 26) | See Table 24 to 26 |
| Total | 100 |

Each test sample was prepared. Observation of appearance changes (visual evaluation) and measurement of color difference (ΔE) were carried out for samples exposed to sunlight (around 80MJ).

Color difference was measured by Lab coordinate system with spectrophotometer. Color difference was calculated based on the color before sunlight exposure. Namely, from the measured value $(L_1, a_1, b_1)$ before sunlight exposure, color difference (ΔE) was calculated by following formula $$\Delta E = \{(L_2-L_1)^2 + (a_2-a_1)^2 + (b_2+b_1)^2\}^{1/2}$$

Table 24 and Table 25 shows the result of combining a single pigment, a pyridazine derivative of the present invention and various sequestering agents.

TABLE 24

| Test Example | Colorant Name | Amount | Sequestering agent Name | Amount | Photostabilizer Amount | Sunlight exposure (80 MJ) ΔE | Appearance |
|---|---|---|---|---|---|---|---|
| 436 | Red No.227 | 0.0001 | — | 0 | 0 | 1.45 | C |
| 437 | (D&C Red No.33) | | | | 0.01 | 0.98 | B |
| 438 | (Trade name: Fast Acid Magenta) | | Trisodium ethylenediamine | 0.02 | 0 | 1.40 | C |
| 439 | | | tetraacetate | | 0.01 | 0.62 | A |
| 440 | | | Sodium metaphosphate | 0.02 | 0 | 1.37 | C |
| 441 | | | | | 0.01 | 0.64 | B |
| 442 | | | Trisodium hydroxyethyl | 0.02 | 0 | 1.43 | C |
| 443 | | | ethylenediamine triacetate | | 0.01 | 0.58 | A |

TABLE 24-continued

| Test Example | Colorant Name | Amount | Sequestering agent Name | Amount | Photostabilizer Amount | Sunlight exposure (80 MJ) ΔE | Appearance |
|---|---|---|---|---|---|---|---|
| 444 | Red No.106 | 0.0001 | — | 0 | 0 | 3.04 | C |
| 445 | (Trade name: Acid Red 52) | | | | 0.02 | 1.23 | B |
| 446 | | | Trisodium ethylenediamine | 0.02 | 0 | 2.98 | C |
| 447 | | | tetraacetate | | 0.02 | 0.84 | A |
| 448 | | | Sodium metaphosphate | 0.02 | 0 | 2.88 | C |
| 449 | | | | | 0.02 | 0.77 | A |
| 450 | | | Sodium polyphosphate | 0.02 | 0 | 2.92 | C |
| 451 | | | | | 0.02 | 0.85 | A |
| 452 | Yellow No.203 | 0.001 | — | 0 | 0 | 2.77 | C |
| 453 | (D&C Yellow No.10) | | | | 0.01 | 0.95 | B |
| 454 | (Trade name: Quinoline Yellow WS) | | Trisodium ethylenediamine | 0.02 | 0 | 2.73 | C |
| 455 | | | tetraacetate | | 0.01 | 0.28 | A |
| 456 | | | Sodium metaphosphate | 0.02 | 0 | 2.74 | C |
| 457 | | | | | 0.01 | 0.22 | A |
| 458 | | | Trisodium hydroxyethyl | 0.02 | 0 | 2.68 | C |
| 459 | | | ethylenediamine triacetate | | 0.01 | 0.25 | A |
| 460 | Yellow No.5 | 0.001 | — | 0 | 0 | 1.83 | C |
| 461 | (FD&C Yellow No.6) | | | | 0.01 | 0.61 | B |
| 462 | (Trade name: Sunset Yellow FCF) | | Trisodium ethylenediamine | 0.02 | 0 | 1.75 | C |
| 463 | | | tetraacetate | | 0.01 | 0.32 | A |
| 464 | | | Sodium metaphosphate | 0.02 | 0 | 1.77 | C |
| 465 | | | | | 0.01 | 0.36 | A |
| 466 | | | Sodium polyphosphate | 0.02 | 0 | 1.75 | C |
| 467 | | | | | 0.01 | 0.33 | A |

Appearance (Evoluation by vision)
A: No change
B: No almost change
C: Yes change

TABLE 25

| Test example | Colorant Name | Amount | Sequestering agent Name | Amount | Photostabilizer Amount | Sunlight exposure (80 MJ) ΔE | Appearance |
|---|---|---|---|---|---|---|---|
| 468 | Blue No. 1 | 0.0001 | — | 0 | 0 | 8.92 | C |
| 469 | (FD & C Blue No. 1) | | | | 0.02 | 1.74 | B |
| 470 | (Trade name: Brilliant Blue FCF) | | Trisodium ethylenediamine | 0.03 | 0 | 8.50 | C |
| 471 | | | tetraacetate | | 0.02 | 1.18 | A |
| 472 | | | Sodium metaphosphate | 0.03 | 0 | 8.02 | C |
| 473 | | | | | 0.02 | 1.00 | A |
| 474 | | | Trisodium hydroxyethyl | 0.03 | 0 | 7.92 | C |
| 475 | | | ethylenediamine triacetate | | 0.02 | 1.08 | A |
| 476 | Green No. 3 | 0.0001 | — | 0 | 0 | 2.12 | C |
| 477 | (FD & C Green No. 3) | | | | 0.02 | 0.75 | B |
| 478 | (Trade name: Fast Green FCF) | | Trisodium ethylenediamine | 0.03 | 0 | 2.08 | C |
| 479 | | | tetraacetate | | 0.02 | 0.48 | A |
| 480 | | | Sodium metaphosphate | 0.03 | 0 | 2.02 | C |
| 481 | | | | | 0.02 | 0.48 | A |
| 482 | | | Sodium polyphosphate | 0.03 | 0 | 2.1 | C |
| 483 | | | | | 0.02 | 0.52 | A |
| 484 | Red No. 213 | 0.0001 | — | 0 | 0 | 3.79 | C |
| 485 | (FD & C Red No. 19) | | | | 0.03 | 2.12 | B |
| 486 | (Trade name: Rhodamine B) | | Trisodium ethylenediamine | 0.05 | 0 | 3.66 | C |
| 487 | | | tetraacetate | | 0.03 | 1.45 | A |
| 488 | | | Sodium metaphosphate | 0.05 | 0 | 3.71 | C |
| 489 | | | | | 0.03 | 1.38 | A |
| 490 | | | Trisodium hydroxyethyl | 0.05 | 0 | 3.72 | C |
| 491 | | | ethylenediamine triacetate | | 0.03 | 1.41 | A |
| 492 | Red No. 401 | 0.001 | — | 0 | 0 | 7.58 | C |
| 493 | (Ext. D & C Red No. 3) | | | | 0.03 | 0.95 | A |
| 494 | (Trade name: Violamine R) | | Trisodium ethylenediamine | 0.1 | 0 | 7.22 | C |
| 495 | | | tetraacetate | | 0.03 | 0.71 | A |
| 496 | | | Sodium metaphosphete | 0.1 | 0 | 7.07 | C |
| 497 | | | | | 0.02 | 0.66 | A |
| 498 | | | Sodium polyphosphate | 0.1 | 0 | 7.14 | C |
| 499 | | | | | 0.02 | 0.78 | A |

Appearance(Evaluation by vision) A: No change B: No almost change C: Yes change

TABLE 26

| Test example | Colorant Name | Amount | Sequestering agent Name | Amount | Photostabilizer Amount | Sunligt exposure (80 MJ) ΔE | Appearance |
|---|---|---|---|---|---|---|---|
| 500 | Red No. 227 | 0.0001 | — | 0 | 0 | 1.59 | C |
| 501 | (Trade name: Fast Acid Magenta) | | | | 0.02 | 1.02 | B |
| 502 | Yellow No. 5 | 0.0001 | Trisodium ethylenediamine tetraacetate | 0.02 | 0 | 1.55 | C |
| 503 | (Trade name: Sunset Yellow FCF) | | | | 0.02 | 0.71 | A |
| 504 | Red No. 227 | 0.0001 | — | 0 | 0 | 3.05 | C |
| 505 | (Trade name: Fast Acid Magenta) | | | | 0.05 | 1.55 | A |
| 506 | Yellow No. 203 | 0.0001 | Sodium metaphosphate | 0.02 | 0 | 3.01 | C |
| 507 | (Trade name: Quinoline Yellow WS) | | | | 0.05 | 1.01 | A |
| 508 | Red No. 106 | 0.00001 | — | 0 | 0 | 3.77 | C |
| 509 | (Trade name: Acid Red 52) | | | | 0.02 | 1.10 | A |
| 510 | Yellow No. 203 | 0.0001 | Trisodium hydroxyethyl ethylenediamine triacetate | 0.02 | 0 | 3.56 | C |
| 511 | (Trade name: Quinoline Yellow WS) | | | | 0.02 | 0.75 | A |
| 512 | Red No. 106 | 0.00001 | — | 0 | 0 | 4.45 | C |
| 513 | (Trade name: Acid Red 52) | | | | 0.02 | 1.33 | B |
| 514 | Yellow No. 5 | 0.0001 | Trisodium ethylenedamine tetraacetate | 0.02 | 0 | 4.26 | C |
| 515 | (Trade name: Sunset Yellow FCF) | | | | 0.02 | 0.98 | A |
| 516 | Yellow No. 203 | 0.0001 | — | 0 | 0 | 1.45 | C |
| 517 | (Trade name: Quinoline Yellow WS | | | | 0.02 | 0.78 | A |
| 518 | Yellow No. 5 | 0.0001 | Sodium metaphosphate | 0.01 | 0 | 1.44 | C |
| 519 | (Trade name: Sunset Yellow FCF) | | | | 0.02 | 0.48 | A |
| 520 | Red No. 213 | 0.00001 | — | 0 | 0 | 3.89 | C |
| 521 | (Trade name: Rhodamine B) | | | | 0.02 | 1.88 | B |
| 522 | Blue No. 1 | 0.00001 | Trisodium hydroxyethyl ethylenediamine triacetate | 0.03 | 0 | 3.85 | C |
| 523 | (Trade name: Brilliant Blue FCF) | | | | 0.02 | 1.22 | A |
| 524 | Red No. 401 | 0.0001 | — | 0 | 0 | 3.04 | C |
| 525 | (Trade name: Violamine R) | | | | 0.02 | 1.36 | A |
| 526 | Blue No. 1 | 0.00001 | Trisodium ethylenediamine tetraecetate | 0.03 | 0 | 3.02 | C |
| 527 | (Trade name: Brilliant Blue FCF) | | | | 0.02 | 0.88 | A |
| 528 | Red No. 401 | 0.0001 | — | 0 | 0 | 4.54 | C |
| 529 | (Trade name: Violamine R) | | | | 0.02 | 1.45 | B |
| 530 | Green No. 3 | 0.00001 | Sodium metaphosphate | 0.03 | 0 | 4.23 | C |
| 531 | (Trade name: Fast Green FCF) | | | | 0.02 | 0.73 | A |

Appearance(Evaluation by vision) A: No change B: No almost change C: Yes change

Tables 24 to 26 show that color difference ΔE for compositions having pyridazine derivative (4,5-dimorpholino-3-hydroxypyridazine) of the present invention and a sequestering agent is very small in comparison with color difference ΔE for other compositions not having a sequestering agent. Also, the change of appearance of the composition is small. Accordingly, it is understood that pyridazine derivatives of the present invention have a better photostabilization effect for pigment when combined with a sequestering agent.

Also, since a sequestering agent itself does not have a photostabilization effect, combining a pyridazine derivative of the present invention and a sequestering agent has synergistic photostabilization effect.

Next, for combinations with sequestering agent, photostabilization effect for each perfume was studied by the following evaluation formulation.

| Formulation for evaluation of perfume stabilization effect (Sequestering agent combination) | |
|---|---|
| Material | Amount (wt %) |
| Ion-exchanged water | to 100 |
| Brucine denatured alcohol | 5 |
| Glycerol | 5 |
| Dipropylene glycol | 5 |
| Polyoxyethylene hydrogenated castor oil | 1 |
| Methyl paraben | 0.2 |
| Lactic acid | 0.006 |
| Sodium lactate | 0.2 |
| Sequestering agent(See Table 27 to 29) | See Table 27 to 29 |
| 4,5-Dimorpholino-3-hydroxypyridazine | See Table 27 to 29 |
| Perfume(See Table 27 to 29) | 0.03 |
| Total | 100 |

Each test sample was prepared. Smell change of samples exposed to sunlight (80MJ) was observed (judgement by perfumier).

Table 27 shows the result of combining natural perfume, a pyridazine derivative of the present invention and various sequestering agents.

TABLE 27

| Test example | Natural perfume Name | Sequestering agent Name | Amount | Photostabilizer Amount | Sunlight exposure(80 MJ) Smell evaluation |
|---|---|---|---|---|---|
| 532 | Rose oil | — | 0 | 0 | C |
| 533 | | | | 0.02 | B |
| 534 | | Trisodium ethylenediamine tetraacetate | 0.03 | 0 | C |
| 535 | | | | 0.02 | A |
| 536 | Jasmine oil | — | 0 | 0 | C |
| 537 | | | | 0.02 | B |
| 538 | | Sodium metaphosphate | 0.03 | 0 | C |
| 539 | | | | 0.02 | A |
| 540 | Lavender oil | — | 0 | 0 | C |
| 541 | | | | 0.02 | B |
| 542 | | Trisodium hydroxyethyl ethylenediamine triacetate | 0.03 | 0 | C |
| 543 | | | | 0.02 | A |
| 544 | Peppermint oil | — | 0 | 0 | C |
| 545 | | | | 0.01 | B |
| 546 | | Trisodium ethylenediamine tetraacetate | 0.03 | 0 | C |
| 547 | | | | 0.01 | A |
| 548 | Orange oil | — | 0 | 0 | C |
| 549 | | | | 0.05 | B |
| 550 | | Sodium metaphosphate | 0.03 | 0 | C |
| 551 | | | | 0.05 | A |
| 552 | Yiang yiang oil | — | 0 | 0 | C |
| 553 | | | | 0.02 | B |
| 554 | | Trisodium hydroxyethyl ethylenediamine triacetate | 0.03 | 0 | C |
| 555 | | | | 0.02 | A |
| 556 | Bergamot oil | — | 0 | 0 | C |
| 557 | | | | 0.05 | B |
| 558 | | Trisodium ethylenediamine tetraacetate | 0.03 | 0 | C |
| 559 | | | | 0.05 | A |
| 560 | Musk oil | — | 0 | 0 | C |
| 561 | | | | 0.1 | B |
| 562 | | Sodium metephosphate | 0.03 | 0 | C |
| 563 | | | | 0.01 | A |

Smell evaluation A: No change B: No almost change C: Yes change

Table 27 shows that smell change of a composition including a pyridazine derivative (4,5-dimorpholino-3-hydroxypyridazine) of the present invention and a sequestering agent is very small in comparison with smell change of other compositions not having sequestering agent. Accordingly, it is understood that a pyridazine derivative of the present invention has a better photostabilization effect for natural perfume by combining it with a sequestering agent.

Also, since the sequestering agent itself does not have a photostabilization effect, combining a pyridazine derivative of the present invention and a sequestering agent has a synergistic photostabilization effect.

Table 28 shows the result of combining a synthetic perfume, a pyridazine derivative of the present invention and various sequestering agents.

TABLE 28

| Test example | Synthetic perfume Name | Sequestering agent Name | Amount | Photostabilizer Amount | Sunlight exposure(80 MJ) Smell evaluation |
|---|---|---|---|---|---|
| 564 | Limonene | — | 0 | 0 | C |
| 565 | | | | 0.02 | B |
| 566 | | Trisodium hydroxyethyl ethylenediamine triacetate | 0.03 | 0 | C |
| 567 | | | | 0.02 | A |
| 568 | cis-3-Hexenol | — | 0 | 0 | C |
| 569 | | | | 0.02 | B |
| 570 | | Trisodium ethylenediamine tetraacetate | 0.03 | 0 | C |
| 571 | | | | 0.02 | A |
| 572 | Citral | — | 0 | 0 | C |
| 573 | | | | 0.01 | B |
| 574 | | Trisodium hydroxyethyl ethylenediamine triacetete | 0.03 | 0 | C |
| 575 | | | | 0.01 | A |
| 576 | β-ionone | — | 0 | 0 | C |
| 577 | | | | 0.01 | B |
| 578 | | Trisodium ethylenediamine tetraacetate | 0.03 | 0 | C |
| 579 | | | | 0.01 | A |
| 580 | Oranthiol | — | 0 | 0 | C |
| 581 | | | | 0.05 | B |
| 582 | | Sodium metaphosphate | 0.03 | 0 | C |

TABLE 28-continued

| Test example | Synthetic perfume Name | Sequestering agent Name | Amount | Photostabilizer Amount | Sunlight exposure(80 MJ) Smell evaluation |
|---|---|---|---|---|---|
| 583 | | | | 0.05 | A |
| 584 | Benzyl benzoate | — | 0 | 0 | C |
| 585 | | | | 0.02 | B |
| 586 | | Trisodium hydroxyethyl ethylenediamine triacetete | 0.03 | 0 | C |
| 587 | | | | 0.02 | A |
| 588 | Rose oxide | — | 0 | 0 | C |
| 589 | | | | 0.05 | B |
| 590 | | Trisodium ethylenediamine tetraacetate | 0.03 | 0 | C |
| 591 | | | | 0.05 | A |
| 592 | Lilial | — | 0 | 0 | C |
| 593 | | | | 0.1 | B |
| 594 | | Sodium metaphosphate | 0.03 | 0 | C |
| 595 | | | | 0.1 | A |

Smell evaluation A: No change B: No almost change C: Yes change

Table 28 shows that smell change of a composition including a pyridazine derivative (4,5-dimorpholino-3-hydroxypyridazine) of the present invention and a sequestering agent is very small in comparison with smell change of other compositions not having a sequestering agent. Accordingly, it is understood that a pyridazine derivative of the present invention has a better photostabilization effect for synthetic perfume by combining it with a sequestering agent.

Also, since the sequestering agent itself does not have a photostabilization effect, combining of a pyridazine derivative of the present invention and a sequestering agent has a synergistic photostabilization effect.

Table 29 shows the result of combining a base perfume, a pyridazine derivative of the present invention and various sequestering agents.

TABLE 29

| Test example | Base perfume Name | Sequestering agent Name | Amount | Photostabilizer Amount | Sunlight exposure(80 MJ) Smell evaluation |
|---|---|---|---|---|---|
| 596 | Rose | — | 0 | 0 | C |
| 597 | | | | 0.02 | B |
| 598 | | Trisodium hydroxyethyl ethylenediamine triacetate | 0.03 | 0 | C |
| 599 | | | | 0.02 | A |
| 600 | Jasmine | — | 0 | 0 | C |
| 601 | | | | 0.02 | B |
| 602 | | Trisodium ethylenediamine tetraacetate | 0.03 | 0 | C |
| 603 | | | | 0.02 | A |
| 604 | Muguet | — | 0 | 0 | C |
| 605 | | | | 0.02 | B |
| 606 | | Sodium metaphosphate | 0.03 | 0 | C |
| 607 | | | | 0.02 | A |
| 608 | Green | — | 0 | 0 | C |
| 609 | | | | 0.01 | B |
| 610 | | Trisodium hydroxyethyl ethylenediamine triacetate | 0.03 | 0 | C |
| 611 | | | | 0.01 | A |
| 612 | Oriental | — | 0 | 0 | C |
| 613 | | | | 0.01 | B |
| 614 | | Trisodium ethylenediamine tetraacetate | 0.03 | 0 | C |
| 615 | | | | 0.01 | A |
| 616 | Fruity | — | 0 | 0 | C |
| 617 | | | | 0.03 | B |
| 618 | | Sodium metaphosphate | 0.03 | 0 | C |
| 619 | | | | 0.03 | A |
| 620 | Aldehyde | — | 0 | 0 | C |
| 621 | | | | 0.05 | B |
| 622 | | Trisodium hydroxyethyl ethylenediamine triacetate | 0.03 | 0 | C |
| 623 | | | | 0.05 | A |
| 624 | Animal | — | 0 | 0 | C |
| 625 | | | | 0.1 | C |
| 626 | | Trisodium ethylenediamine tetraacetate | 0.03 | 0 | C |
| 627 | | | | 0.1 | A |

Smell evaluation A: No change B: No almost change C: Yes change

Table 29 shows that smell change of a composition including a pyridazine derivative (4,5-dimorpholino-3-hydroxypyridazine) of the present invention and a sequestering agent is very small in comparison with smell change of other compositions not having a sequestering agent. Accordingly, it is understood that a pyridazine derivative of the present invention has a better photostabilization effect for base perfume by combining it with a sequestering agent.

Also, since the sequestering agent itself does not have a photostabilization effect, combining a pyridazine derivative of the present invention and a sequestering agent has a synergistic photostabilization effect.

Next, when combined with a sequestering agent, the photostabilization effect and appearance change of a composition for each drug was studied by the following evaluation formulation.

| Formulation for evaluation of drug stabilization effect (Sequestering agent combination) | |
|---|---|
| Material | Amount (wt %) |
| Ion-exchanged water | to 100 |
| Brucine denatured alcohol | 5 |
| Glycerol | 5 |
| Dipropylene glycol | 5 |
| Polyoxyethylene hydrogenated castor oil | 1 |
| Methyl paraben | 0.2 |
| Lactic acid | 0.006 |
| Sodium lactate | 0.2 |
| Sequestering agent (See Table 30) | See Table 30 |
| 4,5-Dimorpholino-3-hydroxypyridazine | See Table 30 |
| Drug (See Table 30) | See Table 30 |
| Total | 100 |

Each test sample was prepared. Appearance change of the samples exposed to sunlight (around (80MJ) was observed (visual evaluation). Also, residual yield of a drug was measured by liquid chromatography.

Next, Table 30 shows the results of combining a drug, a pyridazine derivative of the present invention and various sequestering agents.

Table 30 shows that residual yield of a drug in a composition having a pyridazine derivative (4,5-dimorpholino-3-hydroxypyridazine) of the present invention and a sequestering agent is very small in comparison with residual yield of a drug in other compositions not having a sequestering agent. Accordingly, it is understood that pyridizine derivative of the present invention has a better photostabilization effect for a drug when combined with a sequestering agent.

Also, since a sequestering agent itself does not have a photostabilization effect, combining of pyridazine derivative of the present invention and a sequestering agent has a synergistic photostabilization effect.

The following are examples of external skin preparations of the present invention. These examples do not limit the present invention. Amounts shown are weight percent

EXAMPLE 1

Lotion

| (Alcohol phase) | |
|---|---|
| Ethanol | 10.0 |
| Oleyl alcohol | 0.1 |
| Polyoxyethylene(20) sorbitan monolaurate | 0.5 |
| Polyoxyethylene(15) lauryl ether | 0.5 |
| 4,5-Dimorpholino-3-hydroxypyridazine | 5.0 |
| Antiseptics | q.s. |
| Perfume | q.s. |
| (Water phase) | |
| 1,3-Butylene glycol | 6.0 |
| Glycerol | 4.0 |
| Ion-exchanged water | Balance |

(Manufacturing method)

Each of water phase and alcohol phase was prepared and further mixed.

TABLE 30

| Test example | Drug Name | Amount | Sequestering agent Name | Amount | Photostabilizer Amount | Sunlight exposure(80 MJ) Residual yield (%) | Appearance |
|---|---|---|---|---|---|---|---|
| 628 | Salicylic acid | 0.1 | — | 0 | 0 | 87.6 | C |
| 629 | | | | | 0.03 | 99.2 | B |
| 630 | | | Trisodium ethylenediamine tetraacetate | 0.03 | 0 | 88.0 | C |
| 631 | | | | | 0.03 | 100.1 | A |
| 632 | Dipotassium glycyrrhizinate | 0.05 | — | 0 | 0 | 85.1 | C |
| 633 | | | | | 0.03 | 97.2 | A |
| 634 | | | Sodium metaphosphate | 0.03 | 0 | 85.8 | B |
| 635 | | | | | 0.03 | 100.0 | A |
| 636 | L-ascorbic acid 2-(di-α-tocopheryl hydrogen phosphate) potassium salt | 0.01 | — | 0 | 0 | 69.0 | C |
| 637 | | | | | 0.03 | 98.5 | B |
| 638 | | | Trisodium hydroxyethyl ethylenediamine triacetate | 0.03 | 0 | 70.1 | C |
| 639 | | | | | 0.03 | 99.4 | A |
| 640 | 2-o-α-α-glucopyranosyl-L-ascorbic acid | 2.0 | — | 0 | 0 | 84.7 | B |
| 641 | | | | | 0.03 | 98.3 | A |
| 642 | | | Sodium metaphosphete | 0.03 | 0 | 85.2 | C |
| 643 | | | | | 0.03 | 99.3 | A |
| 644 | Dibutylhydroxytoluene | 0.01 | — | 0 | 0 | 48.0 | C |
| 645 | | | | | 0.03 | 95.8 | B |
| 646 | | | Soduim metaphosphate | 0.03 | 0 | 54.7 | C |
| 647 | | | | | 0.03 | 98.8 | A |

Appearance(Evaluation by vision) A: No change B: No almost change C: Yes change

EXAMPLE 2

Lotion (Alcohol phase)

| | |
|---|---|
| Ethanol | 10.0 |
| Polyoxyethylene(20) oleyl ether | 0.5 |
| Antiseptics | q.s. |
| Perfume | q.s. |

(Water phase)

| | |
|---|---|
| Dipropylene glycol | 6.0 |
| Sorbitol | 4.0 |
| Polyethylene glycol 1500 | 5.0 |
| 4,5-Dimorpholino-3-hydroxypyridazine hydrogen chloride | 20.0 |
| Methyl cellulose | 0.2 |
| Quince seed | 0.1 |
| Ion-exchanged water | Balance |

(Manufacturing method)

A portion of the ion-exchanged water, methyl cellulose and quince seed were mixed with stirring and a viscous liquid was prepared. The rest of the ion-exchanged water and other water phase ingredients were mixed with dissolving. The above-mentioned viscous liquid was added to this and a homogeneous water phase was obtained. The prepared alcohol phase was added to the water phase and was mixed.

EXAMPLE 3

Cream

| | |
|---|---|
| Stearic acid | 5.0 |
| Stearyl alcohol | 4.0 |
| Isopropyl myristate | 18.0 |
| Glyceryl monostearate | 3.0 |
| Propylene glycol | 10.0 |
| 4,5-Dimorpholino-3-hydroxypyridazine | 20.0 |
| Potassium hydroxide | 0.2 |
| Sodium hydrogensulfite | 0.01 |
| Antiseptics | q.s. |
| Perfume | q.s. |
| Ion-exchanged water | Balance |

(Manufacturing method)

Propylene glycol and potassium hydroxide were added to ion-exchanged water and were dissolved. The mixture was heated and was kept at 70° C. (Water phase). A mixture of the other components were melted with heating and was kept at 70° C. (Oil phase). The oil phase was gradually added to the water phase and an emulsion was formed. After it was homogeneously emulsified with a homomixer, which was cooled to 30° C. with sufficient stirring.

EXAMPLE 4

Cream

| | |
|---|---|
| Stearic acid | 6.0 |
| Sorbitan monostearate | 2.0 |
| Polyoxyethylene(20) sorbitan monostearate | 1.5 |
| Propylene glycol | 10.0 |
| 4,5-Dimorpholino-3-hydroxypyridazine | 1.0 |
| Glyceryl trioctanoate | 10.0 |
| Squalene | 5.0 |
| Sodium hydrogensulfite | 0.01 |
| Ethyl paraben | 0.3 |
| Perfume | q.s. |
| Ion-exchanged water | Balance |

(Manufacturing method)

The propylene glycol and 4,5-dimorpholino-3-hydroxypyridazine were added to ion-exchanged water and were dissolved. It was kept at 70° C. with heating (Water phase). A mixture of the other ingredients was melted with heating and was kept at 70° C. (Oil phase). The oil phase was added gradually to the water phase and an emulsion was formed. After it was emulsified homogeneously with a homomixer, it was cooled to 30° C. with sufficient stirring.

EXAMPLE 5

Milky Lotion

| | |
|---|---|
| Stearic acid | 2.5 |
| Cetyl alcohol | 1.5 |
| Petrolatum | 5.0 |
| Liquid paraffin | 10.0 |
| Polyoxyethylene(10) monooleate | 2.0 |
| Polyethylene glycol 1500 | 3.0 |
| Triethanol amine | 1.0 |
| 4,5-Dimorpholino-3-hydroxypyridazine hydrogen chloride | 10.0 |
| Sodium hydrogensulfite | 0.01 |
| Ethyl paraben | 0.3 |
| Carboxyvinylpolymer | 0.05 |
| Perfume | q.s. |
| Ion-exchanged water | Balance |

(Manufacturing method)

Carboxyvinylpolymer was dissolved in a small amount of ion-exchanged water (A phase). Polyethylene glycol 1500, 4,5-dimorpholino-3-hydroxypyridazine hydrochloride and triethanolamine were added to the remainder of the ion-exchanged water, which was dissolved with heating and was kept at 70° C. (Water phase). Mixture of other ingredients was melted with heating and was kept at 70° C. (Oil phase). The oil phase was added to the water phase to form an emulsion was formed. After A phase was added and was homogeneously emulsified with a homomixer, it was cooled at 30° C. with sufficient stirring.

EXAMPLE 6

Gel

| | |
|---|---|
| 95% Ethanol | 10.0 |
| Dipropylene glycol | 15.0 |
| Polyoxyethylene(50) oleyl ether | 2.0 |
| Carboxyvinylpolymer | 1.0 |
| Sodium hydroxide | 0.15 |
| 4,5-Dimorpholino-3-hydroxypyridazine | 2.0 |
| Methyl paraben | 0.2 |
| Perfume | q.s. |
| Ion-exchanged water | Balance |

(Manufacturing method)

Carboxyvinylpolymer was dissolved in ion-exchanged water homogeneously (A phase). 4,5-Dimorpholino-3-hydroxypyridazine and POE (50) oleyl ether were dissolved in 95% ethanol, which was added to A phase. After the ingredients other than sodium hydroxide were added, sodium hydroxide was added thereto, thereby neutralizing the composition and increasing viscosity.

EXAMPLE 7

Essence

| (A phase) | |
|---|---|
| 95% Ethanol | 10.0 |
| Polyoxyethylene(20) octyldodecanol | 1.0 |
| Methyl paraben | 0.15 |
| Pantothenyl ethylether | 0.1 |
| (B phase) | |
| Potassium hydroxide | 0.1 |
| (C phase) | |
| Glycerol | 5.0 |
| Dipropylene glycol | 10.0 |
| Sodium hydrogensulfite | 0.03 |
| Carboxyvinylpolymer | 0.2 |
| 4,5-Dimorpholino-3-hydroxypyridazine | 0.1 |
| Ion-exchanged water | Balance |

(Manufacturing method)

Each of (A phase) and (C phase) was homogeneously dissolved. (C phase) and additive (A phase) were solubilized. Next, (B phase) was added and mixed.

EXAMPLE 8

Pack

| (A phase) | |
|---|---|
| Dipropylene glycol | 5.0 |
| Polyoxyethylene(60) hydrogenated castor oil | 5.0 |
| (B phase) | |
| Olive oil | 5.0 |
| Tocopheryl acetate | 0.2 |
| Ethyl paraben | 0.2 |
| Perfume | 0.2 |
| (C phase) | |
| 4,5-Dimorpholino-3-hydroxypyridazine | 3.0 |
| Sodium hydrogensulfite | 0.03 |
| Polyvinyl alcohol | 13.0 |
| (Saponification degree 90, Polymerization degree 2000) | |
| Ethanol | 7.0 |
| Ion-exchanged water | Balance |

(Manufacturing method)

Each of A phase, (B phase) and (C phase) was homogeneously dissolved. (A phase) was added to (B phase) and was solubilized. Next, (C phase) was added and mixed.

The above-mentioned examples 1 and 7 had an excellent ultraviolet rays prevention effect. Also, in example 1 to 8, skin trouble was not observed at all.

EXAMPLE 9

Milky Lotion

| (Oil phase) | |
|---|---|
| Stearyl alcohol | 1.5 |
| Squalene | 2.0 |
| Petrolatum | 2.5 |
| Hydrogenated liquid lanolin | 1.5 |
| Evening primrose oil | 2.0 |
| Isopropylmyristate | 5.0 |
| Glyceryl monooleate | 2.0 |
| Polyoxyethylene(60) hydrogenated castor oil | 2.0 |
| Tochopheryl acetate | 0.05 |
| Ethyl paraben | 0.2 |
| Butyl paraben | 0.1 |
| Perfume | q.s. |
| (Water phase) | |
| 4,5-Dimorpholino-3-hydroxypyridazine | 1.0 |
| 4,5-Dimorpholino-3-hydroxypyridazine hydrochloride | 1.0 |
| Sodium hydrogensulfite | 0.01 |
| Glycerol | 5.0 |
| Sodium hyaluronate | 0.01 |
| Carboxyvinylpolymer | 0.2 |
| Potassium hydroxide | 0.2 |
| Ion-exchanged water | Balance |

(Manufacturing method)

Each of oil phase and water phase was dissolved at 70° C. Oil phase was mixed with water phase and was emulsified with emulsifier. Next, the result was cooled at 30° C. with a heat exchanger.

The milky lotion of example 9 had an excellent ultraviolet rays prevention effect. Also the skin trouble was not observed.

EXAMPLE 10

Solid Powdery Foundation

| (1) Talc | 15.0 |
|---|---|
| (2) Sericite | 10.0 |
| (3) Spherical nylon powder | 10.0 |
| (4) Porous silicic anhydride powder | 15.0 |
| (5) Boron nitride | 5.0 |
| (6) Titanium dioxide | 5.0 |
| (7) Iron oxide | 3.0 |
| (8) Zinc Stearate | 5.0 |
| (9) 4,5-Dimorpholino-3-hydroxypyridazine | 5.0 |
| (10) Liquid petrolatum | Balance |
| (11) Glyceryl triisooctanoate | 15.0 |
| (12) Sorbitan sesquioleate | 1.5 |
| (13) Antiseptics | q.s. |
| (14) Perfume | q.s. |

(Manufacturing method)

Each of (1) to (8) was mixed with crushing. A mixture of components of (9) to (14) were added thereto and was mixed with agitation. Solid foundation was obtained by forming to the container.

EXAMPLE 11

W/O Emulsion Foundation

| (1) Spherical nylon | 10.0 |
|---|---|
| (2) Porous silicic anhydride powder | 8.0 |
| (3) Titanated mica | 2.0 |
| (4) Silicone treated sericite | 2.0 |
| (5) Silicone treated mica | 12.0 |
| (6) Silicone treated titanium dioxide | 5.0 |
| (7) Silicone treated iron oxide | 2.0 |
| (8) Ion-exchanged water | Balance |

-continued

|  |  |  |
|---|---|---|
| (9) | 4,5-Dimorpholino-3-hydroxypyridazine | 3.0 |
| (10) | Decamethylcyclopentasiloxane | 18.0 |
| (11) | Dimethylpolysiloxane | 5.0 |
| (12) | Squalane | 1.0 |
| (13) | Polyoxyethylene denatured dimethylpolysiloxane | 2.0 |
| (14) | Antiseptics | q.s. |
| (15) | Perfume | q.s. |

(Manufacturing method)

Ingredients (9) to (15) were mixed and were homogeneously dissolved. A crushed (1) to (7) were added thereto and dispersed. (8) was added to this dispersion liquid and was emulsified. A W/O emulsion foundation was obtained by forming to container.

EXAMPLE 12

Face Powder

|  |  |  |
|---|---|---|
| (1) | Talc | Balance |
| (2) | Sericite | 10.0 |
| (3) | Spherical nylon powder | 10.0 |
| (4) | Boron nitride | 5.0 |
| (5) | Iron oxide | 3.0 |
| (6) | Magnesium carbonate | 5.0 |
| (7) | Squalane | 3.0 |
| (8) | Glyceryl triisooctanoate | 2.0 |
| (9) | Sorbitan sesquioleate | 2.0 |
| (10) | 4,5-Dimorpholino-3-hydroxypyridazine | 0.1 |
| (11) | Antiseptics | q.s. |
| (12) | Perfume | q.s. |

(Manufacturing method)

Each ingredient of (1) to (6) was mixed and crushed. Mixture of each ingredient of (7) to (12) was added and mixed with agitation and a face powder was obtained.

EXAMPLE 13

Eye Shadow

|  |  |  |
|---|---|---|
| (1) | Talc | Balance |
| (2) | Mica | 15.0 |
| (3) | Spherical nylon powder | 10.0 |
| (4) | Boron nitride | 5.0 |
| (5) | Iron oxide | 3.0 |
| (6) | Titanium oxide coated mica | 5.0 |
| (7) | Squalane | 3.0 |
| (8) | Glyceryl triiso octanoate | 2.0 |
| (9) | Sorbitan sesquioleate | 2.0 |
| (10) | 4,5-Dimorpholino-3-hydroxypyridazine | 2.0 |
| (11) | Antiseptics | q.s. |
| (12) | Perfume | q.s. |

(Manufacturing method)

Components of (1) to (6) were crushed and mixed. Furthermore, a mixture of the components of (7) to (12) was added thereto, which was mixed with agitation and an eye shadow was obtained.

EXAMPLE 14

Lipstick

|  |  |  |
|---|---|---|
| (1) | Carnauba wax | 0.5 |
| (2) | Candelilla wax | 5.0 |
| (3) | Ceresin | 10.0 |
| (4) | Squalane | Balance |
| (5) | Glyceryl triisostearate | 10.0 |
| (6) | Glyceryl diisostearate | 20.0 |
| (7) | 4,5-Dimorpholino-3-hydroxypyridazine | 1.0 |
| (8) | Macadamia nut fatty acid cholesteryl | 4.0 |
| (9) | Synthetic sodium magnesium silicate | 0.5 |
| (10) | Hydrophobic silica | 0.5 |
| (11) | Ion-exchanged water | 2.0 |
| (12) | Colorant | q.s. |
| (13) | Antiseptics | q.s. |
| (14) | Perfume | q.s. |

(Manufacturing method)

Ingredients (9) and (10) were dispersed to (8) melted at 60° C. (11) was added to this and was stirred sufficiently. This was added to heated and dissolved (1) to (7) and was agitated sufficiently. After (12) to (14) was added thereto which was dispersed with stirring, lipstick was obtained by molding.

Makeup cosmetics of examples 10 to 14 have an excellent ultraviolet ray prevention effect. No skin trouble or no discoloration was observed.

EXAMPLE 15

Hair Form

|  |  |  |
|---|---|---|
| (Formulation for undiluted solution) | | |
| (1) | Acrylic resin/alkanolamine solution (50%) | 8.0 |
| (2) | Polyoxyethylene hydrogenated castor oil | q.s. |
| (3) | Liquid petrolatum | 5.0 |
| (4) | Glycerol | 3.0 |
| (5) | Perfume | q.s. |
| (6) | Antiseptics | q.s. |
| (7) | Ethanol | 15.0 |
| (8) | 4,5-Dimorpholino-3-hydroxypyridazine | 0.01 |
| (9) | Ion-exchanged water | Balance |
| (Formulation for filling) | | |
| (1) | Undiluted solution | 90.0 |
| (2) | Liquefied petroleum gas | 10.0 |

|  |  |  |
|---|---|---|
| (1) | Polyoxypropylene(40) butyl ether | 20.0 |
| (2) | Polyoxyethylene hydrogenated castor oil | 1.0 |
| (3) | Ethanol | 50.0 |
| (4) | Perfume | q.s. |
| (5) | Antiseptics | q.s. |
| (6) | Colorant | q.s. |
| (7) | 4,5-Dimorpholino-3-hydroxypyridazine | 2.0 |
| (8) | Ion-exchanged water | Balance |

(Manufacturing method)

Liquid petrolatum was added to dissolved glycerol and polyoxyethylene hydrogenated castor oil and was homogeneously emulsified with a homomixer. This was added to solution of the other ingredients. After the undiluted solution was filled a can, the valve was fixed and gas was added.

EXAMPLE 16

Hair Liquid

| Example 16 Hair Liquid | |
|---|---|
| (1) Polyoxypropylene(40) butyl ether | 20.0 |
| (2) Polyoxyethylene hydrogenated castor oil | 1.0 |
| (3) Ethanol | 50.0 |
| (4) Perfume | q.s. |
| (5) Antiseptics | q.s. |
| (6) Colorant | q.s. |
| (7) 4,5-Dimorpholino-3-hydroxypyridazine | 2.0 |
| (8) Ion-exchanged water | Balance |

(Manufacturing method)

Polyoxypropylene(40) butyl ether, polyoxyethylene hydrogenated castor oil, 4,5-dimorpholino-3-hydroxypyridadine, perfume and antiseptics were dissolved in ethanol. Colorant was dissolved in ion-exchanged water. Water phase was added to Ethanol phase and was filtered with filter paper.

EXAMPLE 17

Hair Spray

| (Formulation of undiluted solution) | |
|---|---|
| (1) Acrylic resin/alkanolamine solution (50%) | 7.0 |
| (2) Cetyl alcohol | 0.1 |
| (3) Silicone oil | 0.3 |
| (4) Ethanol | Balance |
| (5) Perfume | q.s. |
| (6) 4,5-Dimorpholino-3-hydroxypyridazine | 2.0 |
| (7) Ion-exchanged water | 3.0 |
| (Formulation for filling) | |
| (1) Undiluted solution | 50.0 |
| (2) Liquefied petroleum gas | 50.0 |

(Manufacturing method)

Other ingredients were added to ethanol and dissolved and the result was filtered. After undiluted solution was added to a can and the valve was fixed, gas was added.

EXAMPLE 18

Hair Tonic

| | |
|---|---|
| (1) 4,5-Dimorpholino-3-hydroxypyridazine | 3.0 |
| (2) Hydrogenated castor oil ethyleneoxide(40 mol) additives | 2.0 |
| (3) Ethanol | 60.0 |
| (4) Perfume | q.s. |
| (5) Ion-exchanged water | Balance |

(Manufacturing method)

The hydrogenated castor oil, ethylene oxide (40 moles) additives and 4,5-dimorpholino-3-hydroxypyridazine were dissolved in ethanol. The ethanol phase and water phase were mixed and perfume was added.

The cosmetics for hair and scalp of examples 15 to 18 had an excellent ultraviolet ray prevention effect. Also, scalp trouble and discoloration over of time were not observed.

EXAMPLE 19

Lotion

| (Alcohol phase) | |
|---|---|
| Ethanol | 10.0 |
| Oleyl alcohol | 0.1 |
| Polyoxyethylene(20) sorbitan monolaurate | 0.5 |
| Polyoxyethylene(15) lauryl ether | 0.5 |
| Dibutylhydroxy toluene | 0.01 |
| Antiseptics | q.s. |
| Perfume | q.s. |
| (Water phase) | |
| L-ascorbic acid 2-(dl-α-tocopheryl hydrogen phosphate) potassium salt | 0.02 |
| 4,5-Dimorpholino-3-hydroxypyridazine | 1.0 |
| 1,3-Butylene glycol | 6.0 |
| Glycerol | 4.0 |
| Ion-exchanged water | Balance |

(Manufacturing method)

The water phase and alcohol phase that were prepared individually were mixed.

EXAMPLE 20

Cream

| | |
|---|---|
| Stearic acid | 5.0 |
| Stearyl alcohol | 4.0 |
| Isopropyl myristate | 18.0 |
| Glyceryl monostearate | 3.0 |
| Propylene glycol | 10.0 |
| 4,5-Dimorpholino-3-hydroxypyridazine | 0.1 |
| L-ascorbic acid 2-(dl-α-tocopheryl hydrogen phosphate) potassium salt | 0.01 |
| Potassium hydroxide | 0.2 |
| Dibutylhydroxytoluene | 0.01 |
| Sodium hydrogensulfite | 0.01 |
| Antiseptics | q.s. |
| Perfume | q.s. |
| Ion-exchanged water | Balance |

(Manufacturing method)

Propylene glycol, L-ascorbic acid 2-(dl-α-tocopheryl hydrogen phosphate) potassium salt, 4,5-dimorpholino-3-hydroxypyridazine and potassium hydroxide were added to ion-exchanged water and were dissolved. It was kept with heating at 70° C. (Water phase). Other ingredients were melted with heating and kept at 70° C. (Oil phase). The oil phase was added gradually to the water phase and was emulsified preliminarily. After oil phase was added to water phase and was emulsified homogeneously with a homomixer, it was cooled to 30° C. with sufficient stirring.

EXAMPLE 21

Emulsion

| | |
|---|---|
| Stearic acid | 2.5 |
| Cetyl alcohol | 1.5 |
| Petrolatum | 5.0 |
| Liquid petrolatum | 10.0 |
| Polyoxyethylene(10) monooleate | 2.0 |
| Polyethylene glycol 1500 | 3.0 |

-continued

| | |
|---|---|
| Triethanolamine | 1.0 |
| L-ascorbic acid 2-(dl-α-tocopheryl hydrogen phosphate) potassium salt | 0.01 |
| 4,5-Dimorpholino-3-hydroxypyridazine | 0.1 |
| Dibutylhydroxytoluene | 0.01 |
| Ethyl paraben | 0.3 |
| Carboxyvinylpolymer | 0.05 |
| Perfume | q.s. |
| Ion-exchanged water | Balance |

(Manufacturing method)

Carboxyvinylpolymer was dissolved in a small amount of ion-exchanged water(A phase). Polyethylene glycol 1500, L-ascorbic acid 2-(dl-α-tocopheryl hydrogen phosphate) potassium salt, 4,5-dimorpholino-3-hydroxypyridazine and triethanolamine were added to the remainder of the ion-exchanged water. It was dissolved with heating and was kept at 70° C. (Water phase). A mixture of other ingredients was melted with heating and was kept at 70° C. (Oil phase). The oil phase was added to the water phase and was emulsified preliminary. After A phase was added thereto and was emulsified homogeneously with a homomixer, which was cooled to 30° C. with sufficient stirring.

EXAMPLE 22

Enamel

| | |
|---|---|
| Nitrocellulose (1/2 Second) | 10.0 |
| Alkyd resin | 10.0 |
| Acetyltributyl citrate | 5.0 |
| 4,5-Dimorpholino-3-hydroxypyridazine | 0.1 |
| Ethyl acetate | 20.0 |
| Butyl acetate | 20.0 |
| Ethyl alcohol | 5.0 |
| Toluene | 30.0 |
| Pigment | q.s. |
| Precipitation inhibitor | q.s. |

(Manufacturing method)

Pigment was added to a part of acetyltributyl citrate and a part of alkyd resin and was kneaded well (Pigment part) Other ingredients were mixed and dissolved. The pigment part was added to this, stirred well, and homogeneously disposed.

EXAMPLE 23

Transparent Liquid Shampoo

| | |
|---|---|
| Sodium lauryl polyoxyethylene(3) sulfate (30% Aqueous solution) | 30.0 |
| Sodium lauryl sulfate (30% Aqueous solution) | 10.0 |
| Coconut fatty acid diethanolamide | 4.0 |
| Glycerol | 1.0 |
| 4,5-Dimorpholino-3-hydroxypyridazine | 0.1 |
| Antiseptics | q.s. |
| colorant | q.s. |
| Perfume | q.s. |
| Sequestering agents | q.s. |
| Purified water | Balance |

(Manufacturing method)

Each component was added to a purified water at 70° C. The mixture was homogeneously dissolved and cooled.

EXAMPLE 24

Rinse

| | |
|---|---|
| Silicone oil | 3.0 |
| Liquid petrolatum | 1.0 |
| Cetyl alcohol | 1.5 |
| Stearyl alcohol | 1.0 |
| Stearyltriethyl ammonium chloride | 0.7 |
| 4,5-Dimorpholino 3-hydroxypyridazine | 0.5 |
| Glycerol | 3.0 |
| Antiseptics | q.s. |
| Colorant | q.s. |
| Perfume | q.s. |
| Purified water | Balance |

(Manufacturing method)

Stearyltimethyl ammonium chloride, glycerol and pigment were added to a purified water and was kept at 70° C. (Water phase). Mixed other ingredients were dissolved with heating and was kept at 70° C. (Oil phase). The oil phase was added to the water phase. The mixture was emulsified with a homomixer, which was cooled with stirring.

Pyridazine derivatives and salts thereof of the present invention, as an ultraviolet absorbent absorbs strongly ultraviolet rays of all wavelengths with the range of 290 nm to 400 nm which reach surface of the earth. Accordingly, this absorbent has excellent ultraviolet ray absorption ability. Also, thereof it has high safety and high stability. Also, pyridazine derivatives and salts of the present invention demonstrate an excellent effect as a photostabilizer of colorant, perfume and drug. Especially, by combining a sequestering agent, this effect can be synergistically enhanced. Accordingly, by combining the pyridazine derivative of the present invention, the obtained external preparation for the skin has high ultraviolet rays prevention effect, good stability, good safety and good photostability.

Another use other than for the external skin preparations is an ultraviolet ray absorption composition which has excellent ultraviolet ray prevention effect.

We claim:

1. An ultraviolet absorbent comprising a pyridazine derivative having a formula (1):

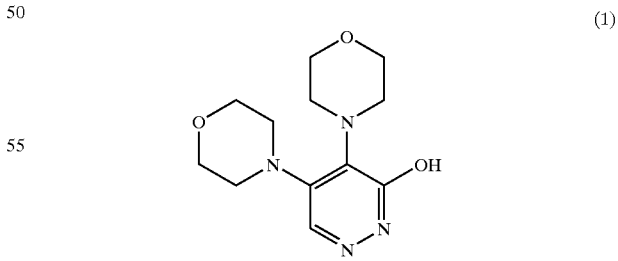

or its salts thereof.

2. An ultraviolet absorptive composition comprising the ultraviolet absorbent according to claim 1.

3. A photostabilizer comprising the pyridazine derivative having a formula (1):

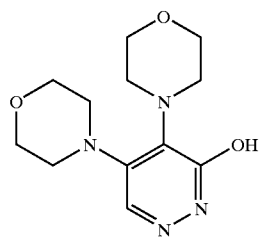

(1)

or its salts thereof.

4. The photostabilizer according to claim 3, wherein said photostabilizer includes a sequestering agent.

5. An external preparation for skin comprising the ultraviolet absorbent according to claim 1.

6. The external skin preparation according to claim 5, wherein said external preparation for skin includes an inorganic powder.

7. An external preparation for skin comprising the photostabilizer according to claim 3.

8. An external preparation for skin comprising the photostabilizer according to claim 4.

9. The external preparation for skin according to claim 5, wherein said external preparation for skin includes 0.001 wt % to 20 wt % of the pyridazine derivative or its salt thereof.

10. The external preparation for skin according to claim 6, wherein said external preparation for skin includes 0.001 wt % to 20 wt % of the pyridazine derivative or its salts thereof.

11. The external preparation of skin according to claim 7, wherein said external preparation for skin includes 0.001 wt % to 20 wt % of the pyridazine derivative or its salt thereof.

12. The external preparation for skin according to claim 8, wherein said external preparation for skin includes 0.001 wt % to 20 wt % of the pyridazine derivative or its salts thereof.

* * * * *